US006235974B1

(12) United States Patent
Qiu et al.

(10) Patent No.: US 6,235,974 B1
(45) Date of Patent: May 22, 2001

(54) HYPERSENSITIVE RESPONSE INDUCED RESISTANCE IN PLANTS BY SEED TREATMENT WITH A HYPERSENSITIVE RESPONSE ELICITOR

(75) Inventors: Dewen Qiu, Seattle; Zhong-Min Wei, Kirkland, both of WA (US); Steven V. Beer, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 08/984,207

(22) Filed: Dec. 3, 1997

Related U.S. Application Data

(60) Provisional application No. 60/033,230, filed on Dec. 5, 1996.

(51) Int. Cl.[7] .............................. A01H 1/00; A01H 5/00; C12N 15/82; C12N 5/00
(52) U.S. Cl. ................................ 800/301; 514/2; 514/12; 800/298; 800/305; 800/306; 800/307; 800/308; 800/309; 800/310; 800/311; 800/312; 800/313; 800/314; 800/315; 800/317; 800/317.1; 800/317.2; 800/317.3; 800/317.4; 800/318; 800/319; 800/320; 800/320.1; 800/320.2
(58) Field of Search .............................. 47/87; 800/278, 800/276, 317.4, 295, 298, 301, 305, 306, 307, 308, 309, 310, 311, 312, 313, 314, 315, 316, 317, 317.1, 317.2, 317.3, 318, 319, 320, 320.1, 320.2, 320.3, 321, 322, 323, 323.1, 323.2, 323.3; 514/2, 12; 435/410, 418

(56) References Cited

U.S. PATENT DOCUMENTS

| | | |
|---|---|---|
| 4,569,841 | 2/1986 | Liu .................................... 424/93.4 |
| 4,597,972 | 7/1986 | Taylor .................................... 426/36 |
| 4,601,842 | 7/1986 | Caple et al. ............................ 252/70 |
| 4,740,593 | 4/1988 | Gonzalez et al. ........................ 422/1 |
| 4,851,223 | 7/1989 | Sampson ............................... 424/711 |
| 4,886,825 | 12/1989 | Ruess et al. ........................... 514/383 |
| 4,931,581 | 6/1990 | Schurter et al. ........................ 560/18 |
| 5,057,422 | 10/1991 | Bol et al. .............................. 800/298 |
| 5,061,490 | 10/1991 | Paau et al. ........................... 424/93.47 |
| 5,135,910 | 8/1992 | Blackburn et al. ....................... 514/2 |
| 5,173,403 | 12/1992 | Tang ..................................... 435/6 |
| 5,217,950 | 6/1993 | Blackburn et al. ....................... 514/2 |
| 5,243,038 | 9/1993 | Ferrari et al. ........................ 536/23.1 |
| 5,244,658 | 9/1993 | Parke .................................. 504/117 |
| 5,260,271 | 11/1993 | Blackburn et al. ....................... 514/2 |
| 5,348,743 | 9/1994 | Ryals et al. ........................... 424/94.61 |
| 5,494,684 | 2/1996 | Cohen .................................. 424/523 |
| 5,523,311 | 6/1996 | Schurter et al. ....................... 514/361 |
| 5,550,228 | 8/1996 | Godiard et al. ........................ 800/298 |
| 5,552,527 | 9/1996 | Godiard et al. ........................ 530/379 |
| 5,650,387 | 7/1997 | Wei et al. .............................. 514/2 |
| 5,708,139 | * 1/1998 | Collmer et al. . |
| 5,849,868 | * 12/1998 | Beer et al. . |
| 5,850,015 | 12/1998 | Bauer et al. ........................... 800/279 |
| 6,001,959 | 12/1999 | Bauer et al. ........................... 530/300 |

FOREIGN PATENT DOCUMENTS

| | | |
|---|---|---|
| 0 612 848 A3 | 8/1994 | (EP) . |
| WO 93/23532 | 11/1993 | (WO) . |
| WO 94/01546 | 1/1994 | (WO) . |
| WO 94/26782 | 11/1994 | (WO) . |
| WO 95/19443 | 7/1995 | (WO) . |
| WO 96/39802 | 12/1996 | (WO) . |
| WO 98/15547 | 4/1998 | (WO) . |
| WO 98/24297 | 6/1998 | (WO) . |
| WO 98/32844 | 7/1998 | (WO) . |
| WO 98/37752 | 9/1998 | (WO) . |
| WO 98/54214 | 12/1998 | (WO) . |
| WO 99/07206 | 2/1999 | (WO) . |
| WO 99/07207 | 2/1999 | (WO) . |

OTHER PUBLICATIONS

Qui et al., "Treatment of Tomato Seed with Harpin Enhances Germination and Growth and Induces Resistance to *Ralstonia Solanacearum*," *Phytopathology*, 87:6, S80 (1997).

Burr et al., "Increased Potato Yields by Treatment of Seedpieces with Specific Strains of Pseudomonas Fluorescens And *P. putida*," *Phytopathology*, 68:1377–1383 (1978).

Ricci et al., "Proteinaceous Elicitors of Plant Defense Responses," B. Fritig eds., *Mechanisms of Plant Defense Responses*, Netherlands, pp. 121–130 (1993).

Keen et al., "Syringolide Elicitors Specified By Avirulence Gene D Alleles In *Pseudomonas Syringae*," *Advances in Molecular Genetics of Plant–Microbe Interactions*, 3:41–48 (1994).

Klessig et al., "The Salicylic Acid Signal In Plants," *Plant Molecular Biology*, 26:1439–1458 (1994).

Bogdanove et al., "Unified Nomenclature For Broadly Conserved hrp Genese of Phytopathogenic Bacteria," *Molecular Microbiology*, 20(3):681–683 (1996).

Bonnet et al., "Acquired Resistance Triggered By Elicitins In Tobacco and Other Plants," *European Journal of Plant Pathology*, 102:181–192 (1996).

(List continued on next page.)

*Primary Examiner*—Paula Hutzell
*Assistant Examiner*—Ousama M-Faiz Zaghmout
(74) *Attorney, Agent, or Firm*—Nixon Peabody LLP

(57) ABSTRACT

The present invention relates to a method of imparting pathogen resistance to plants. This involves applying a hypersensitive response elicitor polypeptide or protein in a non-infectious form to a plant seed under conditions where the polypeptide or protein contacts cells of the plant seed. The present invention is also directed to a pathogen resistance imparting plant seed. Alternatively, transgenic plant seeds containing a DNA molecule encoding a hypersensitive response elicitor polypeptide or protein can be planted in soil and a plant can be propagated from the planted seed under conditions effective to impart pathogen resistance to the plant.

36 Claims, No Drawings

OTHER PUBLICATIONS

Cui et al., "The RsmA⁻ Mutants of *Erwinia carotovora* subsp. *carotovora* Strain Ecc71 Overexpress hrpN$_{Ecc}$ and Elicit a Hypersensitive Reaction–like Response in Tobacco Leaves," *Molecular Plant–Microbe Interactions*, 9(7):565–573 (1996).

Gopalan et al., "Bacterial Genes Involved in the Elicitation of Hypersensitive Response and Pathogenesis," *Plant Disease*, 80(6):604–610 (1996).

Hoffland et al., "Comparison of Systemic Resistance Induced by Avirulent and Nonpathogenic Pseudomonas Species," *Phytopathology*, 86(7):757–762 (1996).

Ryals et al., "Systemic Acquired Resistance," *The Plant Cell*, 8:1809–1819 (1996).

Wei et al., "Induced Systemic Resistance to Cucumber Dieseases and Increased Plant Growth by Plant Growth–Promoting Rhizobacteria Under Field Conditions," *Phytopathology*, 86:221–224 (1996).

Wengelnik et al., "Expression and Localization of HrpA1, a Protein of *Xanthomonas campestris* pv. vesicatoria Essential for Pathogenicity and Induction of the Hypersensitive Reaction," *Journal of Bacteriology*, 178:1061–1069 (1996).

Inbar et al., "Elicitors of Plant Defensive Systems Reduce Insect Densities and Disease Incidence," *Journal of Chemical Ecology*, 24(1):135–149 (1998).

Jin et al., "A Truncated Fragment of Harpin$_{Pss}$ Induces Systemic Resistance To *Xanthomonas Campetris* pv. Oryzae In Rice," *Physiological and Molecular Plant Pathology*, 51:243–257 (1997).

Collmer et al., "*Erwinia chyrsanthemi* and *Pseudomonas syringae*: Plant Pathogens Trafficking in Extracellular Virulence Proteins," pp. 43–78.

Frederick et al., "The WTS Water–Soaking Genes of *Erwinia stewartii* are Related to hrp Genes," Seventh International Symposium on Molecular Plant Microbe Interactions, Abstract No. 191 (Jun. 1994).

Wei et al., "Proteinaceous Elicitors of the Hypersensitive Response from *Xanthomonas campestris* pv. glycines," Seventh International Symposium on Molecular Plant Microbe Interactions, Abstract No. 244 (Jun. 1994).

Preston et al., "The HrpZ Proteins of *Pseudomonas syringae* pvs. syringae, glycinea, and tomato are Encoded by an Operon Containing Yersinia ysc Homologs and Elicit the Hypersensitive Response in Tomato but not Soybean," *Mol. Plant–Microbe Interact.*, 8(5):717–32 (1995).

Bauer et al., "*Erwinia chrysanthemi* hrp Genes and their Involvement in Elicitation of the Hypersensitive Response in Tobacco," Sixth International Symposium on Molecular Plant microbe Interactions, Abstract No. 146 (Jul. 1992).

Stryer, L., "Enzymes are Highly Specific," *Biochemistry*, San Francisco: W.H. Freeman and Company, p. 116 (1975).

Keen et al., "Inhibition of the Hypersensitive Reaction of Soybean Leaves to Incompatible Pseudomonas spp. by *Blasticidin S*, streptomycin or Elevated Temperature," *Physiological Plant Pathology*, 18:325–37 (1981).

Lerner, R.A., "Tapping the Immunological Repertoire to Produce Antibodies of Predetermined Specificity," *Nature*, 299:592–96 (1982).

Staskawicz et al., "Cloned Avirulence Gene of *Pseudomonas Syringae* pv. *glycinea* Determines Race–specific Incompatibility on *Glycine mas* (L.) Merr.," *Proc. Natl. Acad. Sci.*, 81:6024–28 (1984).

Bauer et al., "*Erwinia chrysanthemi* Harpin$_{Ech}$: An Elicitor of the Hypersensitive Response that Contributes to Soft–Rot Pathogenesis," *MPMI*, 8(4):484–91 (1995).

Huang et al., "Characterization of the Hrp Cluster from *Pseudomonas syringae* pv. *syringae* 61 and TnphoA Tagging of Genes Encoding Exported or Membrane–Spanning Hrp Proteins," *Molec. Plant–Microbe Interact.*, 4(5):469–76 (1991).

Huang et al., "The *Pseudomonas syringae* pv. *syringae* 61 hrpH Product, an Envelope Protein Required for Elicitation of the Hypersensitive Response in Plants," *J. Bacteriol.*, 174(21):6878–85 (1992).

Bonas, U., "hrp Genes of Phytopathogenic Bacteria," *Current Topics in Microbio.*, 192:79–98 (1994).

Arlat et al., "PopA1, A Protein Which Induces a Hypersensitivity–Like Response in Specific Protein Petunia Genotypes, is Secreted via the Hrp Pathway of *Pseudomonas solanacearum*," *The EMBO J.*, 13(3):543–53 (1994).

Kessmann et al., "Induction of Systemic Acquired Disease Resistance in Plants By Chemicals," *Ann. Rev. Phytopathol.*, 32:439–59 (1994).

Kelman, A., "The Relationship of Pathogenicity in *Pseudomonas Solanacearum* To Colony Appearance on a Tetrazolium Medium," *Phytopathology*, 44:693–95 (1954).

Winstead et al., "Inoculation Techniques For Evaluating Resistance to *Pseudomonas Solanacearum*," *Phytopathology*, 42:628–34 (1952).

Ahl et al., "Iron Bound–Siderophores, Cyanic Acid, and Antibiotics Involved in Suppression of *Thielaviopsis basiocola* by a *Pseudomonas fluorescens* Strain," *J. Phytopathology*, 116:121–34 (1986).

Anderson et al., "Responses of Bean to Root Colonization with *Pseudomonas putida* in a Hydroponic System," *Phytopathology*, 75(9):992–95 (1985).

Gardner et al., "Growth Promotion and Inhibition by Antibiotic–Producing Fluorescent Pseudomonads on Citrus Roots," *Plant and Soil*, 77:103–13 (1984).

Kloepper, J.W., "Effect of Seed Piece Inoculation with Plant Growth–Promoting Rhizobacteria on Populations of *Erwinia carotovora* on Potato Roots and In Daughter Tubers," *Phytopathology*, 73(2):217–19 (1983).

Atkinson et al., "The Hypersensitive Reaction of Tobacco to *Pseudomonas Syringae* pv. pisi ¹," *Plant Physiol.*, 79:843–47 (1985).

Huynh et al., "Bacterial Blight of Soybean: Regulation of a Pathogen Gene Determining Host Cultivar Specificity," *Science*, 245:1374–77 (1986).

Kloepper et al., "Plant Growth–Promoting Rhizobacteria on Canola (Rapeseed)," *Plant Disease* 72(1):42–6 (1988).

Kloepper et al., "Enhanced Plant Growth by Siderophores Produced by Plant Growth–Promoting Rhizobacteria," *Nature*, 286:885–86 (1980).

Kloepper et al., "Pseudomonas Siderophores: A Mechanism Explaining Disease–Suppressive Soils," *Current Microbiology*, 4:317–20 (1980).

Kloepper et al., "Emergence–Promoting Rhizobacteria: Description and Implications for Agriculture," In: *Iron, Siderophores, and Plant Disease*, Swinborne (ed), Plenum, NY, 155–64 (1986).

Kloepper et al., "Relationships of in vitro Antibiotics of Plant Growth–Promoting Rhizobacteria to Plant Growth and the Displacement of Root Microflora," *Phytopathology*, 71(10):1020–24 (1981).

Kloepper et al., "Effects of Rhizosphere Colonization by Plant Growth–Promoting Rhizobacteria on Potato Plant Development and Yield," *Phytopathology*, 70(11):1078–82 (1980).

Kloepper et al., "Plant Growth Promotion Mediated byRhizosphere Bacterial Colonizers,"In: *The Rhizosphere and Plant Growth*, Keister et al. (eds), pp. 315–26 (1991).

Lifshitz et al., "Growth Promotion of Canola (rapeseed) Seedlings by a Strain of *Pseudomonas putida* Under Gnotobiotic Conditions," *Microbiol.* 33:390–95 (1987).

Liu et al., "Induction of Systemic Resistance in Cucumber Against Bacterial Angular Leaf Spot by Plant Growth–Promoting Rhizobacteria," *Phytopathology*, 85(8):843–47 (1995).

Loper et al., "Influence of Bacterial Sources of Indole–3–aceticc Acid on Root Elongation of Sugar Beet," *Phytopathology*, 76(4):386–89 (1986).

Schroth et al., "Disease–Suppressive Soil and Root–Colonizing Bacteria," *Science*, 216:1376–81 (1982).

Stutz et al., "Naturally Occurring Fluorescent Pseudomonads Involved Suppression of Black Root Rot of Tobacco," *Phytopathology*, 76(2):181–85 (1986).

Lindgren et al., "Gene Cluster of *Pseudomonas Syringae* pv. "Phaseolicola" Controls Pathogenicity of Bean Plants and Hypersensitivity on Nonhost Plants," *J. Bacteriol.* 168(2):512–22 (1986).

Bauer et al., "Cloning of a Gene from *Erwinia Amylovora* Involved in Induction of Hypersensitivity and Pathogenicity," *Plant Pathogenic Bacteria*, Proceedings of the Sixth International Conference on Plant Pathogenic Bacteria, Maryland pp. 425–29 (1987).

Wei et al., "Induction of Systemic Resistance of Cucumber to *Colletotrichum orbiculare* by Select Strains of Plant Growth–Promoting Rhizobacteria," *Phytopathology*, 81:1508–12 (1991).

Wei et al., "Induction of Systemic Resistance with Seed Treatment by PGPR Strains," pp. 191–194.

Weller, D.M., "Biological Control of Soilborne Plant Pathogens in the Rhizosphere with Bacteria," *Ann. Rev. Phytopathol.*, 26:379–407 (1988).

young et al., "PGPR: Is There a Relationship Between Plant Growth Regulators and the Stimulation of Plant Growth or Biological Activity?," pp. 182–186.

Wei et al., "Induced Systemic Resistance by Select Plant Growth–Promoting Rhizobacteria Against Bacterial Wilt of Cucumber and the Beetle Vectors," *Phytopathology*, 86:1154, Abstract No. 313 (1995).

Wieringa–Brants et al., Induced Resistance in Hypersensitive Tobacco Against Tobacco Mosaic Virus by Injection of Intercellular Fluid from Tobacco Plants with Systemic Acquired Resistance, *Phytopathology*, 118:165–70 (1987).

Malamy et al., "Salicylic Acid: A Likely Endogenous Signal in the Resistance Response of Tobacco to Viral Infection," *Science*, 250:1002–04 (1990).

Dean et al., "Immunisation Against Disease: The Plant Fights Back," pp. 383–411.

Cameron et al., "Biologically Induced Systemic Acquired Resistance in *Arabidopsis thaliana*," *The Plant Journal*, 5(5):715–25 (1994).

Laby et al., "Structural and Functional Analysis of *Erwinia Amylovora* Harpin, An Elicitor of the Plant Hypersensitive Response," *Phytopathology*, 84:345 (1994).

Van Gijsegem et al., "Evolutionary Conservation of Pathogenicity Determinants Among Plant and Animal Pathogenic Bacteria," *Trends Micorbiol.*, 1:175–80 (1993).

Kamoun, et al., "Extracellular Protein Elicitors from Phytophthora: Host–Specificity and Induction of Resistance to Bacterial and Fungal Phytopathogens," *Molecular Plant–Microbe Interactions*, 6(1):15–25 (1993).

Baillieul, et al., "A New Elicitor of the Hypersensitive Response in Tobacco: A Fungal Glycoprotein Elicits Cell Death, Expression of Defence Genes, Production of Salicylic Acid, and Induction of Systemic Acquired Resistance," *The Plant J*, 8(4):551–60 (1995).

Collinge et al., "Plant Gene Expression in Response to Pathogens," *Plant Molecular Biology*, 9:389–410 (1987).

Shatzman et al., "Expression, Identification, and Characterization of Recombinant Gene Products in *Escherichia coli,*" *Methods in Enzymology*, 152:661–73 (1987).

Tenhaken, et al., "Function of the Oxidative Burst in Hypersensitive Disease Resistance," *Proc. Natl. Acad. Sci. USA*, 92:4158–63 (1995).

Bonnet, et al., "Induction de nécroses foliaires, de protéines b et de résistance dans les interactions tabac Phytophthora," 6(9):829–37 (1986).

Gallitelli, et al., "Satellite–Mediated Protection of Tomato Against Cucumber Mosaic Virus: II. Field Test Under Natural Epidemic Conditions in Southern Italy," *Plant Disease*, 75(1):93–5 (1991).

Ahn, et al., "Effects of Chilling Periods on the Growth and Yield of Strawberry (*Fragaria grandifloro* EHRH) in Forcing Culture," *Res. Rept. RDA (Hort.)*, 27(1):17–26 (1985).

Montasser, et al., "Satellite–Mediated Protection of Tomato Against Cucumber Mosaic Virus: I. Greenhouse Experiments and Simulated Epidemic Conditions in the Field," *Plant Disease*, 75(1):86–92 (1991).

Marks, R.J., "Varietal Resistance to Potato Cyst Nematode," *Agricultural Entomology*, pp. 63–67 (1979).

Walton, et al., "Host–Selective Toxins and Disease Specificity: Perspectives and Progress," *Annu. Rev. Phytopathol.*, 31:275–303 (1993).

Atkinson, M.M., "Molecular Mechanisms of Pathogen Recognition by Plants," *Advances in Plant Pathology*, 10:36–64 (1993).

Godiard, et al., "Differential Regulation in Tobacco Cell Suspensions of Genes Involved in Plant–Bacteria Interactions by Pathogen–Related Signals," *Plant Molecular Biology*, 17:409–13 (1991).

Ricci, et al., "Structure and Activity of Proteins from Pathogenic Fungi Phytophthora Eliciting Necrosis and Acquired Resistance in Tobacco," *Eur. J. Biochem.*, 183:555–63 (1989).

Lakhmatova, I.T., "Induction of Plant Resistance to Viral Diseases: Application of Vaccination," *Sel'skokhozyaistvennaya Biologiya* 3:39–51 (1991).

*Biologicheskii Zhurnal Armenii*, 31(3):305–09 (1978).

Lakhmatova, I.T., "Using Biologically Active Substances to Induced Plant Resistance to Viruses Immunization," *Biologiya*, 3:13–22 (1992).

Shields, R., "Towards Insect–Resistant Plants," *Nature*, 328:12–13 (1987).

Huang et al., "Molecular Cloning of a *Pseudomonas syringae* pv. *syringae* Gene Cluster That Enables *Pseudomonas fluorescens* To Elicit the Hypersensitive Response in Tobacco Plants," *J. Bacteriol.*, 170(10):4748–56 (1988).

Ricci, et al., "Differential Production of Parasiticein, an Elicitor of Necrosis and Resistance in Tobacco, by Isolates of *Phytophthora parasitica,*" *Plant Pathology*, 41:298–307 (1992).

Honée, et al., "Molecular Characterization of the Interaction Between the Fungal Pathogen *Cladosporium Fulvum* and Tomato," *Advances in Molecular Genetics of Plant–Microbe Interactions*, 3:199–206 (1994).

Keller, et al., "Responses of Tobacco to Elicitins, Proteins From Phytophthora Spp. Eliciting Acquired Resistance," *Advances in Molecular Genetics of Plant–Microbe Interactions*, 3:327–32 (1994).

Keen, et al., "Bacteria Expressing Avirulence Gene D Produce a Specific Elicitor of the Soybean Hypersensitive Reaction," *Molecular Plant–Microbe Interactions*, 3(2):112–21 (1990).

Bauer, et al., "*Erwinia chrysanthemi hrp* Genes and Their Involvement in Soft Rot Pathogenesis and Elicitation of the Hypersensitive Response," *MPMI*, 7(5):573–81 (1994).

Schottens–Toma et al., "Purification and Primary Structure of a Necrosis–inducing Peptide from the Apoplastic Fluids of Tomato Infected with *Cladosporium fulvum* (syn. *Fulvia fulva*)," *Physiological and Molecular Plant Pathology*, 33:59–67 (1988).

Steinberger et al., "Creation and Complementation of Pathogenicity Mutants of *Erwinia Amylovora,*" *Molecular Plant–Microbe Interactions*, 1(3):135–44 (1988).

Beer et al., "The Hypersensitive Response is Elicited by *Escherichia Coli* Containing a Cluster of Pathogenicity Genes from *Erwinia Amylovora,*" *Phytopathology*, 79(10):1156 (Abstract 169) (1989).

Hiatt et al., "Production of Antibodies in Transgenic Plants," *Nature*, 342:76–8 (1989).

Hippe et al., "In Situ Localization of a Foreign Protein in Transgenic Plants by Immunoelectron Microscopy Following High Pressure Freezing. Freeze Substitution and Low Temperature Embedding," *European Journal of Cell Biology*, 50:230–34(1989).

Huang et al., "Isolation and Purification of a Factor from *Pseudomonas solanacearum* That Induces a Hypersensitive– like Response in Potato Cells," *Molecular Plant–Microbe Interactions*, 2(3):132–38 (1989).

James et al., "Genetic Transformation of Apple (*Malus pumila* Mill.) Using a Disarmed Ti–binary Vector," *Plant Cell Reports*, 7:658–61 (1989).

Laby et al., "Cloning and Preliminary Characterization of an HRP Gene Cluster of *Erwinia Amylovora,*" *Phytopathology*, 79(10):1211 (Abstract 607) (1989).

Dow et al., "Extracellular Proteases from *Xanthomonas campestris* pv. Campestris, the Black Rot Pathogen," *Applied and Environmental Microbiology*, 56(10):2994–98 (1990).

Walters et al., "Gene for Pathogenicity and Ability to Cause the Hypersensitive Reaction Cloned from *Erwinia Aaylovora,*" *Physiological and Molecular Plant Pathology*, 36:509–21 (1990).

Wu et al., "Cloning, Genetic Organization, and Characterization of a Structural Gene Encoding Bacillopeptidase F from *Bacillus subtilis,*" *The Journal of Biological Chemistry*, 265(12):6845–50 (1990).

Bauer et al., "Further Characterization of an hrp Gene Cluster of *Erwinia amylovora,*" *Molecular Plant–Microbe Interactions* 4(5):493–99 (1991).

Beer et al., "The HRP Gene Cluster of *Erwinia amylovora,*" *Advances in Molecular Genetics of Plant–Microbe Interactions*, 1:53–60 (1991).

Benvenuto et al., "'Phytoantibodies': A General Vector for the Expression of Immunoglobulin Domains in Transgenic Plants," *Plant Molecular Biology*, 17:865–74 (1991).

Milat et al., "Physiological and Structural Changes in Tobacco Leaves Treated with Cryptogein, a Proteinaceous Elicitor from *Phytophthora cryptogea,*" *Phytopathology*, 81(11):1364–68 (1991).

Ruberti et al., "A Novel Class of Plant Proteins Containing a Homeodomain with a Closely Linked Leucine Zipper Motif," *The EMBO Journal*, 10(7):1787–91 (1991).

Quigley et al., "Nucleotide Sequence and Expression of a Novel Glycine–Rich Protein Gene from *Arabidopsis thaliana,*" *Plant Molecular Biology*, 17:949–52 (1991).

van Kan et al., "Cloning and Characterization of cDNA of Avirulence Gene avr9 of the Fungal Pathogen *Cladosporium fulvum*, Casual Agent of Tomato Leaf Mold," *Molecular Plant–Microbe Interactions*, 4(1):52–9 (1991).

Waldmann, T.A., "Monoclonal Antibodies in Diagnosis and Therapy," *Science*, 252:1657–62 (1991).

Willis et al., "hrp Genes of Phytopathogenic Bacteria," *Molecular Plant–Microbe Interactions*, 4:(2) 132–38 (1991).

Beer et al., "Are Harpins Universal Elicitors of the Hypersensitive Response of Phytopathogenic Bacteria?," *Advances in Molecular Genetics of Plant–Microbe Interactions*, 2:281–86 (1992).

Laby et al., "Hybridization and Functional Complementation of the hrp Gene Cluster from *Erwinia amylovora* Strain Ea321 with DNA of Other Bacteria," *Molecular Plant–Microbe Interactions*, 5(5):412–19 (1992).

Sandhu, "Protein Engineering of Antibodies," *Crit. Rev. in Biotech.*, (92—review) 12(5/6):437–62 (1992).

Wei et al., "Harpin, Elicitor of the Hypersensitive Response Produced by the Plant Pathogen *Erwinia amylovora,*" *Science*, 257:85–8 (1992).

He et al., "*Pseudomonas syringae* pv. *syringae* Harpin$_{pss}$: A Protein that is Secreted via the Hrp Pathway and Elicits the Hypersensitive Response in Plants," *Cell*, 73:1255–66 (1993).

Bonas, U., "Bacterial Home Goal by Harpins," *Trends in Microbiology*, 2:1–2 (1994).

Boccara, et al., "Plant Defense Elicitor Protein Produced by *Erwinia chrysanthemi,*" *Mechanisms of Plant Defense Responses*, p. 166 (1993).

Alfano et al., "Analysis of the Role of the *Pseudomonas Syringae* pv. *Syringae* HrpZ Harpin in Elicitation of the Hypersensitive Response in Tobacco Using Functionally Non–Polar hrpZ Deletion Mutations, Truncated HrpZ Fragments, and hrmA Mutations," *Molecular Microbiology*, 19(4):715–728 (1996).

Linthorst et al., "Constitutive Expression of Pathogenesis–Related Proteins PR–1, GRP, and PR–S in Tobacco Has No Effect on Virus Infection," *The Plant Cell*, 1:285–291 (1989).

Lorang et al., "Characterization of avrE from *Pseudomonas syringae* pv. Tomato: A hrp–Linked Avirulence Locus Consisting Of at Least Two Transcriptional Units," *MPMI* 8(1):49–57 (1995).

Malamy et al., "Salicylic Acid and Plant Disease Resistance," *The Plant Journal*, 2(5):643–654 (1992).

McGurl et al., "Structure, Expression, and Antisense Inhibition of the Systemin Precursor Gene," *Science*, 255:1570–1573 (1992).

Nissinen et al., "*Clavibacter Michiganensis* Subsp. *Sepedonicus* Elicits a Hypersensitive Response in Tobacco and Secretes Hypersensitive Response–Inducing Protein," *Phytopathology*, 87:678–684 (1997) (Abstract only).

Kloepper et al., "Enhanced Plant Growth by Siderophores Produced by Plant Growth–promoting Rhizobacteria," *Nature* 286:885–886 (1980).

Wu et al. Plant Cell. 1995. Sep. issue. vol. 7: 1357–1368, 1995.*

Yu. et al. Proc. Natl. Acad. Sci. 1995. May 9 issue. vol. 92: 4088–4094, 1995.*

Huang et al. 1992. Nov. issue. vol.174:6878–6885. (Journal of Bacteriology), 1992.*

Baillieul et al. Plant Journal. 1995. vol. 8:551–560, 1995.*

Schulte et al. J. Bacteriol. 1992. Feb. issue. vol. 174: 815–823, 1992.*

* cited by examiner

HYPERSENSITIVE RESPONSE INDUCED RESISTANCE IN PLANTS BY SEED TREATMENT WITH A HYPERSENSITIVE RESPONSE ELICITOR

This application claims the benefit of U.S. Provisional Patent Application Serial No. 60/033,230, filed Dec. 5, 1996.

This invention was made with support from the U.S. Government under USDA NRI Competitive Research Grant No. 91-37303-6430.

FIELD OF THE INVENTION

The present invention relates to imparting hypersensitive response induced resistance to plants by treatment of seeds.

BACKGROUND OF THE INVENTION

Living organisms have evolved a complex array of biochemical pathways that enable them to recognize and respond to signals from the environment. These pathways include receptor organs, hormones, second messengers, and enzymatic modifications. At present, little is known about the signal transduction pathways that are activated during a plant's response to attack by a pathogen, although this knowledge is central to an understanding of disease susceptibility and resistance. A common form of plant resistance is the restriction of pathogen proliferation to a small zone surrounding the site of infection. In many cases, this restriction is accompanied by localized death (i.e., necrosis) of host tissues. Together, pathogen restriction and local tissue necrosis characterize the hypersensitive response. In addition to local defense responses, many plants respond to infection by activating defenses in uninfected parts of the plant. As a result, the entire plant is more resistant to a secondary infection. This systemic acquired resistance can persist for several weeks or more (R. E. F. Matthews, *Plant Virology* (Academic Press, New York, ed. 2, 1981)) and often confers cross-resistance to unrelated pathogens (J. Kuc, in *Innovative Approaches to Plant Disease Control*, I. Chet, Ed. (Wiley, New York, 1987), pp. 255–274, which is hereby incorporated by reference). See also Kessman, et al., "Induction of Systemic Acquired Disease Resistance in Plants By Chemicals," *Ann. Rev. Phytopathol.* 32:439–59 (1994), Ryals, et al., "Systemic Acquired Resistance," *The Plant Cell* 8:1809–19 (Oct. 1996), and Neuenschwander, et al., "Systemic Acquired Resistance," *Plant-Microbe Interactions* vol. 1, G. Stacey, et al. ed. pp. 81–106 (1996), which are hereby incorporated by reference.

Expression of systemic acquired resistance is associated with the failure of normally virulent pathogens to ingress the immunized tissue (Kuc, J., "Induced Immunity to Plant Disease," *Bioscience*, 32:854–856 (1982), which is hereby incorporated by reference). Establishment of systemic acquired resistance is correlated with systemic increases in cell wall hydroxyproline levels and peroxidase activity (Smith, J. A., et al., "Comparative Study of Acidic Peroxidases Associated with Induced Resistance in Cucumber, Muskmelon and Watermelon," *Physiol. Mol. Plant Pathol.* 14:329–338 (1988), which is hereby incorporated by reference) and with the expression of a set of nine families of so-called systemic acquired resistance gene (Ward, E. R., et al., "Coordinate Gene Activity in Response to Agents that Induce Systemic Acquired Resistance," *Plant Cell* 3:49–59 (1991), which is hereby incorporated by reference). Five of these defense gene families encode pathogenesis-related proteins whose physiological functions have not been established. However, some of these proteins have antifungal activity in vitro (Bol, J. F., et al., "Plant Pathogenesis-Related Proteins Induced by Virus Infection," *Ann. Rev. Phytopathol.* 28:113–38 (1990), which is hereby incorporated by reference) and the constitutive expression of a bean chitinase gene in transgenic tobacco protects against infection by the fungus *Rhizoctonia solani* (Broglie, K., et al., "Transgenic Plants with Enhanced Resistance to the Fungal Pathogen Rhizoctonia Solani," *Science* 254:1194–1197 (1991), which is hereby incorporated by reference), suggesting that these systemic acquired resistance proteins may contribute to the immunized state (Uknes, S., et al., "Acquired Resistance in Arabidopsis," *Plant Cell* 4:645–656 (1992), which is hereby incorporated by reference).

Salicylic acid appears to play a signal function in the induction of systemic acquired resistance since endogenous levels increase after immunization (Malamy, J., et al., "Salicylic Acid: A Likely Endogenous Signal in the Resistance Response of Tobacco to Viral Infection," *Science* 250:1002–1004 (1990), which is hereby incorporated by reference) and exogenous salicylate induces systemic acquired resistance genes (Yalpani, N., et al., "Salicylic Acid is a Systemic Signal and an Inducer of Pathogenesis-Related Proteins in Virus-Infected Tobacco," *Plant Cell* 3:809–818 (1991), which is hereby incorporated by reference), and acquired resistance (Uknes, S., et al., "Acquired Resistance in Arabidopsis," *Plant Cell* 4:645–656 (1992), which is hereby incorporated by reference). Moreover, transgenic tobacco plants in which salicylate is destroyed by the action of a bacterial transgene encoding salicylate hydroxylase do not exhibit systemic acquired resistance (Gaffney, T., et al., "Requirement of Salicylic Acid for the Induction of Systemic Acquired Resistance," *Science* 261:754–56 (1993), which is hereby incorporated by reference). However, this effect may reflect inhibition of a local rather than a systemic signal function, and detailed kinetic analysis of signal transmission in cucumber suggests that salicylate may not be essential for long-distance signaling (Rasmussen, J. B., et al., "Systemic Induction of Salicylic Acid Accumulation in Cucumber after Inoculation with *Pseudomonas Syringae* pv. *Syringae*," *Plant Physiol.* 97:1342–1347) (1991), which is hereby incorporated by reference).

Immunization using biotic agents has been extensively studied. Green beans were systemically immunized against disease caused by cultivar-pathogenic races of *Colletotrichum lindemuthianum* by prior infection with either cultivar-nonpathogenic races (Rahe, J. E., "Induced Resistance in *Phaseolus Vulgaris* to Bean Anthracnose," *Phytopathology* 59:1641–5 (1969); Elliston, J., et al., "Induced Resistance to Anthracnose at a Distance from the Site of the Inducing Interaction," *Phytopathology* 61:1110-12 (1971); Skipp, R., et al., "Studies on Cross Protection in the Anthracnose Disease of Bean," *Physiological Plant Pathology* 3:299–313 (1973), which are hereby incorporated by reference), cultivar-pathogenic races attenuated by heat in host tissue prior to symptom appearance (Rahe, J. E., et al., "Metabolic Nature of the Infection-Limiting Effect of Heat on Bean Anthracnose," *Phytopathology* 60:1005–9 (1970), which is hereby incorporated by reference) or nonpathogens of bean. The anthracnose pathogen of cucumber, *Colletotrichum lagenarium*, was equally effective as non-pathogenic races as an inducer of systemic protection against all races of bean anthracnose. Protection was induced by *C. lagenarium* in cultivars resistant to one or more races of *C. lindemuthianum* as well as in cultivars susceptible to all reported races of the fungus and which accordingly had been referred to as 'lacking genetic resistance' to the pathogen (Elliston, J., et al., "Protection of Bean Against Anthracnose by Colletotrichum Species Nonpathogenic on Bean," *Phytopathologische Zeitschrift* 86:117–26 (1976); Elliston, J., et al., "A Comparative Study on the Development of Compatible, Incompatible and Induced Incompatible Interactions Between Collectotrichum Species and *Phaseolus Vulgaris,*" *Phytopathologische Zeitschrift* 87:289–303 (1976), which are hereby incorporated by reference). These results suggest that the same mechanisms may be induced in cultivars reported as 'possessing' or 'lacking' resistance genes (Elliston, J., et al., "Relation of Phytoalexin Accumulation to Local and Systemic Protection of Bean Against Anthracnose," *Phytopathologische Zeitschrift* 88:114–30 (1977), which is hereby incorporated by reference). It also is apparent that cultivars susceptible to all races of *C. lindemuthianum* do not lack genes for induction of resistance mechanisms against the pathogen.

Kuc, J., et al., "Protection of Cucumber Against *Collectotrichum Lagenarium* by *Colletotrichum Lagenarium,*" *Physiological Plant Pathology* 7:195–9 (1975), which is hereby incorporated by reference), showed that cucumber plants could be systemically protected against disease caused by *Colletotrichum lagenarium* by prior inoculation of the cotyledons or the first true leaf with the same fungus. Subsequently, cucumbers have been systemically protected against fungal, bacterial, and viral diseases by prior localized infection with either fungi, bacteria, or viruses (Hammerschmidt, R., et al., "Protection of Cucumbers Against *Colletotrichum Lagenarium* and *Cladosporium Cucumerinum,*" *Phytopathology* 66:790–3 (1976); Jenns, A. E., et al., "Localized Infection with Tobacco Necrosis Virus Protects Cucumber Against *Colletotrichum Lagenarium,*" *Physiological Plant Pathology* 11:207–12 (1977); Caruso, F. L., et al. "Induced Resistance of Cucumber to Anthracnose and Angular Leaf Spot by *Pseudomonas Lachrymans* and *Colletotrichum Lagenarium,*" *Physiological Plant Pathology* 14:191–201 (1979); Staub, T., et al., "Systemic Protection of Cucumber Plants Against Disease Caused by *Cladosporium Cucumerinum* and *Colletotrichum Lagenarium* by Prior Localized Infection with Either Fungus," *Physiological Plant Pathology*, 17:389–93 (1980); Bergstrom, G. C., et al., "Effects of Local Infection of Cucumber by *Colletotrichum Lagenarium, Pseudomonas Lachrymans* or Tobacco Necrosis Virus on Systemic Resistance to Cucumber Mosaic Virus," *Phytopathology* 72:922–6 (1982); Gessler, C., et al., "Induction of Resistance to Fusarium Wilt in Cucumber by Root and Foliar Pathogens," *Phytolathology* 72:1439–41 (1982); Basham, B., et al., "Tobacco Necrosis Virus Induces Systemic Resistance in Cucumbers Against *Sphaerotheca Fuliginea,*" *Physiological Plant Pathology* 23:137–44 (1983), which are hereby incorporated by reference). Non-specific protection induced by infection with *C. lagenarium* or tobacco necrosis virus was effective against at least 13 pathogens, including obligatory and facultative parasitic fungi, local lesion and systemic viruses, wilt fungi, and bacteria. Similarly, protection was induced by and was also effective against root pathogens. Other curcurbits, including watermelon and muskmelon have been systemically protected against *C. lagenarium* (Caruso, F. L., et al., "Protection of Watermelon and Muskmelon Against *Colletotrichum Lagenarium* by *Colletotrichum Lagenarium,*" *Phytopathology* 67:1285–9 (1977), which is hereby incorporated by reference).

Systemic protection in tobacco has also been induced against a wide variety of diseases (Kuc, J., et al., "Immunization for Disease Resistance in Tobacco," *Recent Advances in Tobacco Science* 9:179–213 (1983), which is hereby incorporated by reference). Necrotic lesions caused by tobacco mosaic virus enhanced resistance in the upper leaves to disease caused by the virus (Ross, A. F., et al., "Systemic Acquired Resistance Induced by Localized Virus Infections in Plants," *Virology* 14:340–58 (1961); Ross, A. F., et al., "Systemic Effects of Local Lesion Formation," *In: Viruses of Plants* pp. 127–50 (1966), which are hereby incorporated by reference). *Phytophthora parasitica* var. *nicotianae*, *P. tabacina* and *Pseudomonas tabaci* and reduced reproduction of the aphid *Myzus persicae* (McIntyre, J. L., et al., "Induction of Localized and Systemic Protection Against *Phytophthora Parasitica* var. *nicotianae* by Tobacco Mosaic Virus Infection of Tobacco Hypersensitive to the Virus," *Physiological Plant Pathology* 15:321–30 (1979); McIntyre, J. L., et al., "Effects of Localized Infections of *Nicotiana Tabacum* by Tobacco Mosaic Virus on Systemic Resistance Against Diverse Pathogens and an Insect," *Phytopathology* 71:297–301 (1981), which are hereby incorporated by reference). Infiltration of heat-killed *Pseudomonas tabacin* (Lovrekovich, L., et al., "Induced Reaction Against Wildfire Disease in Tobacco Leaves Treated with Heat-Killed Bacteria," *Nature* 205:823–4 (1965), which is hereby incorporated by reference), and *Pseudomonas solanacearum* (Sequeira, L, et al., "Interaction of Bacteria and Host Cell Walls: Its Relation to Mechanisms of Induced Resistance," *Physiological Plant Pathology* 10:43–50 (1977), which is hereby incorporated by reference), into tobacco leaves induced resistance against the same bacteria used for infiltration. Tobacco plants were also protected by the nematode *Pratylenchus penetrans* against *P. parasitica* var. *nicotiana* (McIntyre, J. L., et al. "Protection of Tobacco Against *Phytophthora Parasitica* Var. *Nicotianae* by Cultivar-Nonpathogenic Races, Cell-Free Sonicates and *Pratylenchus Penetrans,*" *Phytopathology* 68:235–9 (1978), which is hereby incorporated by reference).

Cruikshank, I. A. M., et al., "The Effect of Stem Infestation of Tobacco with *Peronospora Tabacina* Adam on Foliage Reaction to Blue Mould," *Journal of the Australian Institute of Agricultural Science* 26:369–72 (1960), which is hereby incorporated by reference, were the first to report immunization of tobacco foliage against blue mould (i.e., *P. tabacina*) by stem injection with the fungus, which also resulted in dwarfing and premature senescence. It was recently discovered that injection external to the xylem not only alleviated stunting but also promoted growth and development. Immunized tobacco plants, in both glasshouse and field experiments, were approximately 40% taller, had a 40% increase in dry weight, a 30% increase in fresh weight, and 4–6 more leaves than control plants (Tuzun, S., et al., "The Effect of Stem Injections with *Peronospora Tabacina* and Metalaxyl Treatment on Growth of Tobacco and Protection Against Blue Mould in the Field," *Phytopathology* 74:804 (1984), which is hereby incorporated by reference). These plants flowered approximately 2–3 weeks earlier than control plants (Tuzun, S., et al., "Movement of a Factor in Tobacco Infected with *Peronospora Tabacina* Adam which Systemically Protects Against Blue Mould," *Physiological Plant Pathology* 26:321–30 (1985), which is hereby incorporated by reference).

Systemic protection does not confer absolute immunity against infection, but reduces the severity of the disease and delays symptom development. Lesion number, lesion size, and extent of sporulation of fungal pathogens are all decreased. The diseased area may be reduced by more than 90%.

When cucumbers were given a 'booster' inoculation 3–6 weeks after the initial inoculation, immunization induced by C. lagenarium lasted through flowering and fruiting (Kuc, J., et al., "Aspects of the Protection of Cucumber Against *Colletotrichum Lagenarium* by *Colletotrichum Lagenarium*," Phytopathology 67:533–6 (1977), which is hereby incorporated by reference). Protection could not be induced once plants had set fruit. Tobacco plants were immunized for the growing season by stem injection with sporangia of *P. tabacina*. However, to prevent systemic blue mould development, this technique was only effective when the plants were above 20 cm in height.

Removal of the inducer leaf from immunized cucumber plants did not reduce the level of immunization of pre-existing expanded leaves. However, leaves which subsequently emerged from the apical bud were progressively less protected than their predecessors (Dean, R. A., et al., "Induced Systemic Protection in Cucumber: Time of Production and Movement of the 'Signal'," Phytopathology 76:966–70 (1986), which is hereby incorporated by reference). Similar results were reported by Ross, A. F., "Systemic Effects of Local Lesion Formation," In: *Viruses of Plants* pp. 127–50 (1966), which is hereby incorporated by reference, with tobacco (local lesion host) immunized against tobacco mosaic virus by prior infection with tobacco mosaic virus. In contrast, new leaves which emerged from scions excised from tobacco plants immunized by stem-injection with *P. tabacina* were highly protected (Tuzun, S., et al., "Transfer of Induced Resistance in Tobacco to Blue Mould (Peronospora tabacina Adam.) Via Callus," Phytopathology 75:1304 (1985), which is hereby incorporated by reference). Plants regenerated via tissue culture from leaves of immunized plants showed a significant reduction in blue mould compared to plants regenerated from leaves of non-immunized parents. Young regenerants only showed reduced sporulation. As plants aged, both lesion development and sporulation were reduced. Other investigators, however, did not reach the same conclusion, although a significant reduction in sporulation in one experiment was reported (Lucas, J. A., et al., "Nontransmissibility to Regenerants from Protected Tobacco Explants of Induced Resistance to *Peronospora Hyoscyami*," Phytopathology 75:1222–5 (1985), which is hereby incorporated by reference).

Protection of cucumber and watermelon is effective in the glasshouse and in the field (Caruso, F. L., et al., "Field Protection of Cucumber Against *Colletotrichum Lagenarium* by *C. Lagenarium*," Phytopathology 67:1290–2 (1977), which is hereby incorporated by reference). In one trial, the total lesion area of *C. lagenarium* on protected cucumber was less than 2% of the lesion areas on unprotected control plants. Similarly, only 1 of 66 protected, challenged plants died, whereas 47 of 69 unprotected, challenged watermelons died. In extensive field trials in Kentucky and Puerto Rico, stem injection of tobacco with sporangia of *P. tabacina* was at least as effective in controlling blue mould as the best fungicide, metalaxyl. Plants were protected, leading to a yield increase of 10–25% in cured tobacco.

Induced resistance against bacteria and viruses appears to be expressed as suppression of disease symptoms or pathogen multiplication or both (Caruso, F. L., et al., "Induced Resistance of Cucumber to Anthracnose and Angular Leaf Spot by *Pseudomonas Lachrymans* and *Colletotrichum Lagenarium*," Physiological Plant Pathology* 14:191–201 (1979); Doss, M., et al., "Systemic Acquired Resistance of Cucumber to *Pseudomonas Lachrymans* as Expressed in Suppression of Symptoms, but not in Multiplication of Bacteria, " *Acta Phytopatholoqia Academiae Scientiarum Hungaricae* 16: (3–4), 269–72 (1981); Jenns, A. E., et al., "Non-Specific Resistance to Pathogens Induced Systemically by Local Infection of Cucumber with Tobacco Necrosis Virus, *Colletotrichum Lagenarium* or *Pseudomonas Lachrymans*," *Phytopathologia Mediterranea* 18:129–34 (1979), which are hereby incorporated by reference).

As described above, research concerning systemic acquired resistance involves infecting plants with infectious pathogens. Although studies in this area are useful in understanding how systemic acquired resistance works, eliciting such resistance with infectious agents is not commercially useful, because such plant-pathogen contact can weaken or kill plants. The present invention is directed to overcoming this deficiency.

SUMMARY OF THE INVENTION

The present invention relates to a method of producing plant seeds which impart pathogen resistance to plants grown from the seeds. This method involves applying a hypersensitive response elicitor polypeptide or protein in a non-infectious form to plant seeds under conditions where the polypeptide or protein contacts cells of the plant seeds.

As an alternative to applying a hypersensitive response elicitor polypeptide or protein to plant seeds in order to impart pathogen resistance to plants grown from the seeds, transgenic seeds can be utilized. This involves providing a transgenic plant seed transformed with a DNA molecule encoding a hypersensitive response elicitor polypeptide or protein and planting that seed in soil. A plant is then propagated from the planted seed under conditions effective to impart pathogen resistance to the plant.

Another aspect of the present invention relates to a pathogen-resistance imparting plant seed to which a non-infectious hypersensitive response elicitor polypeptide or protein has been applied.

The present invention has the potential to: treat plant diseases which were previously untreatable; treat diseases systemically that one would not want to treat separately due to cost; and avoid the use of agents that have an unpredictable effect on the environment and even the plants. The present invention can impart resistance without using agents which are harmful to the environment or pathogenic to the plant seeds being treated or to plants situated near the location that treated seeds are planted. Since the present invention involves use of a natural product that is fully and rapidly biodegradable, the environment would not be contaminated.

DETAILED DESCRIPTION OF THE INVENTION

The present invention relates to a method of producing plant seeds which impart pathogen resistance to plants grown from the seeds. This method involves applying a hypersensitive response elicitor polypeptide or protein in a non-infectious form to a plant seed under conditions effective to impart disease resistance to a plant grown from the seed.

As an alternative to applying a hypersensitive response elicitor polypeptide or protein to plant seeds in order to impart pathogen resistance to plants grown from the seeds, transgenic seeds can be utilized. This involves providing a transgenic plant seed transformed with a DNA molecule encoding a hypersensitive response elicitor polypeptide or protein and planting that seed in soil. A plant is then propagated from the planted seed under conditions effective to impart pathogen resistance to the plant.

Another aspect of the present invention relates to a pathogen-resistance imparting plant seed to which a non-infectious hypersensitive response elicitor polypeptide or protein has been applied.

The hypersensitive response elicitor polypeptide or protein utilized in the present invention can correspond to hypersensitive response elicitor polypeptides or proteins derived from a wide variety of fungal and bacterial pathogens. Such polypeptides or proteins are able to elicit local necrosis in plant tissue contacted by the elicitor.

Examples of suitable bacterial sources of polypeptide or protein elicitors include Erwinia, Pseudomonas, and Xanthamonas species (e.g., the following bacteria: *Erwinia amylovora, Erwinia chrysanthemi, Erwinia stewartii, Erwinia carotovora, Pseudomonas syringae, Pseudomonas solancearum, Xanthomonas campestris*, or mixtures thereof).

An example of a fungal source of a hypersensitive response elicitor protein or polypeptide is Phytophthora. Suitable species of such fungal pathogens include *Phytophthora parasitica, Phytophthora cryptogea, Phytophthora cinnamomi, Phytophthora capsici, Phytophthora megasperma*, and *Phytophthora citrophthora*.

The embodiment of the present invention where the hypersensitive response elicitor polypeptide or protein is applied to the plant seed can be carried out in a number of ways, including: 1) application of an isolated elicitor polypeptide or protein; 2) application of bacteria which do not cause disease and are transformed with genes encoding a hypersensitive response elicitor polypeptide or protein; and 3) application of bacteria which cause disease in some plant species (but not in those to which they are applied) and naturally contain a gene encoding the hypersensitive response elicitor polypeptide or protein. In addition, seeds in accordance with the present invention can be recovered from plants which have been treated with a hypersensitive response elicitor protein or polypeptide in accordance with the present invention.

In one embodiment of the present invention, the hypersensitive response elicitor polypeptides or proteins to be applied can be isolated from their corresponding organisms and applied to plants. Such isolation procedures are well known, as described in Arlat, M., F. Van Gijsegem, J. C. Huet, J. C. Pemollet, and C. A. Boucher, "PopA1, a Protein which Induces a Hypersensitive-like Response in Specific Petunia Genotypes is Secreted via the Hrp Pathway of *Pseudomonas solanacearum*," EMBO J. 13:543–553 (1994); He, S. Y., H. C. Huang, and A. Collmer, "*Pseudomonas syringae* pv. *syringae* Harpinp$_{Pss}$: a Protein that is Secreted via the Hrp Pathway and Elicits the Hypersensitive Response in Plants," Cell 73:1255–1266 (1993); and Wei, Z.-M., R. J. Laby, C. H. Zumoff, D. W. Bauer, S.-Y. He, A. Collmer, and S. V. Beer, "Harpin Elicitor of the Hypersensitive Response Produced by the Plant Pathogen *Erwinia amylovora*, Science 257:85–88 (1992), which are hereby incorporated by reference. See also pending U.S. patent application Ser. Nos. 08/200,024 and 08/062,024, which are hereby incorporated by reference. Preferably, however, the isolated hypersensitive response elicitor polypeptides or proteins of the present invention are produced recombinantly and purified as described below.

In other embodiments of the present invention, the hypersensitive response elicitor polypeptide or protein of the present invention can be applied to plant seeds by applying bacteria containing genes encoding the hypersensitive response elicitor polypeptide or protein. Such bacteria must be capable of secreting or exporting the polypeptide or protein so that the elicitor can contact plant seed cells. In these embodiments, the hypersensitive response elicitor polypeptide or protein is produced by the bacteria after application to the seeds or just prior to introduction of the bacteria to the seeds.

In one embodiment of the bacterial application mode of the present invention, the bacteria to be applied do not cause the disease and have been transformed (e.g., recombinantly) with genes encoding a hypersensitive response elicitor polypeptide or protein. For example, *E. coli*, which do not elicit a hypersensitive response in plants, can be transformed with genes encoding a hypersensitive response elicitor polypeptide and other related proteins required for production and secretion of the elicitor which is then applied to plant seeds. Expression of this polypeptide or protein can then be caused to occur. Bacterial species (other than *E. coli*) can also be used in this embodiment of the present invention.

In another embodiment of the bacterial application mode of the present invention, the bacteria do cause disease and naturally contain a gene encoding a hypersensitive response elicitor polypeptide or protein. Examples of such bacteria are noted above. However, in this embodiment these bacteria are applied to plant seeds for plants which are not susceptible to the disease carried by the bacteria. For example, *Erwinia amylovora* causes disease in apple or pear but not in tomato. However, such bacteria will elicit a hypersensitive response in tomato. Accordingly, in accordance with this embodiment of the present invention, *Erwinia amylovora* can be applied to tomato seeds to impart pathogen resistance without causing disease in plants of that species.

The hypersensitive response elicitor polypeptide or protein from *Erwinia chrysanthemi* has an amino acid sequence corresponding to SEQ. ID. No. 1 as follows:

```
Met Gln Ile Thr Ile Lys Ala His Ile Gly Gly Asp Leu Gly Val Ser
1               5                   10                  15

Gly Leu Gly Ala Gln Gly Leu Lys Gly Leu Asn Ser Ala Ala Ser Ser
            20                  25                  30

Leu Gly Ser Ser Val Asp Lys Leu Ser Ser Thr Ile Asp Lys Leu Thr
        35                  40                  45

Ser Ala Leu Thr Ser Met Met Phe Gly Gly Ala Leu Ala Gln Gly Leu
    50                  55                  60

Gly Ala Ser Ser Lys Gly Leu Gly Met Ser Asn Gln Leu Gly Gln Ser
65                  70                  75                  80
```

-continued

```
Phe Gly Asn Gly Ala Gln Gly Ala Ser Asn Leu Leu Ser Val Pro Lys
                85                  90                  95
Ser Gly Gly Asp Ala Leu Ser Lys Met Phe Asp Lys Ala Leu Asp Asp
            100                 105                 110
Leu Leu Gly His Asp Thr Val Thr Lys Leu Thr Asn Gln Ser Asn Gln
        115                 120                 125
Leu Ala Asn Ser Met Leu Asn Ala Ser Gln Met Thr Gln Gly Asn Met
    130                 135                 140
Asn Ala Phe Gly Ser Gly Val Asn Asn Ala Leu Ser Ser Ile Leu Gly
145                 150                 155                 160
Asn Gly Leu Gly Gln Ser Met Ser Gly Phe Ser Gln Pro Ser Leu Gly
                165                 170                 175
Ala Gly Gly Leu Gln Gly Leu Ser Gly Ala Gly Ala Phe Asn Gln Leu
            180                 185                 190
Gly Asn Ala Ile Gly Met Gly Val Gly Gln Asn Ala Ala Leu Ser Ala
        195                 200                 205
Leu Ser Asn Val Ser Thr His Val Asp Gly Asn Asn Arg His Phe Val
    210                 215                 220
Asp Lys Glu Asp Arg Gly Met Ala Lys Glu Ile Gly Gln Phe Met Asp
225                 230                 235                 240
Gln Tyr Pro Glu Ile Phe Gly Lys Pro Glu Tyr Gln Lys Asp Gly Trp
                245                 250                 255
Ser Ser Pro Lys Thr Asp Asp Lys Ser Trp Ala Lys Ala Leu Ser Lys
            260                 265                 270
Pro Asp Asp Asp Gly Met Thr Gly Ala Ser Met Asp Lys Phe Arg Gln
        275                 280                 285
Ala Met Gly Met Ile Lys Ser Ala Val Ala Gly Asp Thr Gly Asn Thr
    290                 295                 300
Asn Leu Asn Leu Arg Gly Ala Gly Gly Ala Ser Leu Gly Ile Asp Ala
305                 310                 315                 320
Ala Val Val Gly Asp Lys Ile Ala Asn Met Ser Leu Gly Lys Leu Ala
                325                 330                 335
Asn Ala
```

This hypersensitive response elicitor polypeptide or protein has a molecular weight of 34 kDa, is heat stable, has a glycine content of greater than 16%, and contains substantially no cysteine. The *Erwinia chrysanthemi* hypersensitive response elicitor polypeptide or protein is encoded by a DNA molecule having a nucleotide sequence corresponding to SEQ. ID. No. 2 as follows:

```
CGATTTTACC CGGGTGAACG TGCTATGACC GACAGCATCA CGGTATTCGA CACCGTTACG    60
GCGTTTATGG CCGCGATGAA CCGGCATCAG GCGGCGCGCT GGTCGCCGCA ATCCGGCGTC   120
GATCTGGTAT TTCAGTTTGG GGACACCGGG CGTGAACTCA TGATGCAGAT TCAGCCGGGG   180
CAGCAATATC CCGGCATGTT GCGCACGCTG CTCGCTCGTC GTTATCAGCA GGCGGCAGAG   240
TGCGATGGCT GCCATCTGTG CCTGAACGGC AGCGATGTAT TGATCCTCTG GTGGCCGCTG   300
CCGTCGGATC CCGGCAGTTA TCCGCAGGTG ATCGAACGTT TGTTTGAACT GGCGGGAATG   360
ACGTTGCCGT CGCTATCCAT AGCACCGACG GCGCGTCCGC AGACAGGGAA CGGACGCGCC   420
CGATCATTAA GATAAAGGCG GCTTTTTTTA TTGCAAAACG GTAACGGTGA GGAACCGTTT   480
CACCGTCGGC GTCACTCAGT AACAAGTATC CATCATGATG CCTACATCGG GATCGGCGTG   540
GGCATCCGTT GCAGATACTT TTGCGAACAC CTGACATGAA TGAGGAAACG AAATTATGCA   600
AATTACGATC AAAGCGCACA TCGGCGGTGA TTTGGGCGTC TCCGGTCTGG GGCTGGGTGC   660
```

-continued

```
TCAGGGACTG AAAGGACTGA ATTCCGCGGC TTCATCGCTG GGTTCCAGCG TGGATAAACT    720
GAGCAGCACC ATCGATAAGT TGACCTCCGC GCTGACTTCG ATGATGTTTG GCGGCGCGCT    780
GGCGCAGGGG CTGGGCGCCA GCTCGAAGGG GCTGGGGATG AGCAATCAAC TGGGCCAGTC    840
TTTCGGCAAT GGCGCGCAGG GTGCGAGCAA CCTGCTATCC GTACCGAAAT CCGGCGGCGA    900
TGCGTTGTCA AAAATGTTTG ATAAAGCGCT GGACGATCTG CTGGGTCATG ACACCGTGAC    960
CAAGCTGACT AACCAGAGCA ACCAACTGGC TAATTCAATG CTGAACGCCA GCCAGATGAC   1020
CCAGGGTAAT ATGAATGCGT TCGGCAGCGG TGTGAACAAC GCACTGTCGT CCATTCTCGG   1080
CAACGGTCTC GGCCAGTCGA TGAGTGGCTT CTCTCAGCCT TCTCTGGGGG CAGGCGGCTT   1140
GCAGGGCCTG AGCGGCGCGG GTGCATTCAA CCAGTTGGGT AATGCCATCG GCATGGGCGT   1200
GGGGCAGAAT GCTGCGCTGA GTGCGTTGAG TAACGTCAGC ACCCACGTAG ACGGTAACAA   1260
CCGCCACTTT GTAGATAAAG AAGATCGCGG CATGGCGAAA GAGATCGGCC AGGTTATGGA   1320
TCAGTATCCG GAAATATTCG GTAAACCGGA ATACCAGAAA GATGGCTGGA GTTCGCCGAA   1380
GACGGACGAC AAATCCTGGG CTAAAGCGCT GAGTAAACCG GATGATGACG GTATGACCGG   1440
CGCCAGCATG GACAAATTCC GTCAGGCGAT GGGTATGATC AAAAGCGCGG TGGCGGGTGA   1500
TACCGGCAAT ACCAACCTGA ACCTGCGTGG CGCGGGCGGT GCATCGCTGG GTATCGATGC   1560
GGCTGTCGTC GGCGATAAAA TAGCCAACAT GTCGCTGGGT AAGCTGGCCA ACGCCTGATA   1620
ATCTGTGCTG GCCTGATAAA GCGGAAACGA AAAAAGAGAC GGGGAAGCCT GTCTCTTTTC   1680
TTATTATGCG GTTTATGCGG TTACCTGGAC CGGTTAATCA TCGTCATCGA TCTGGTACAA   1740
ACGCACATTT TCCCGTTCAT TCGCGTCGTT ACGCGCCACA ATCGCGATGG CATCTTCCTC   1800
GTCGCTCAGA TTGCGCGGCT GATGGGGAAC GCCGGGTGGA ATATAGAGAA ACTCGCCGGC   1860
CAGATGGAGA CACGTCTGCG ATAAATCTGT GCCGTAACGT GTTTCTATCC GCCCCTTTAG   1920
CAGATAGATT GCGGTTTCGT AATCAACATG GTAATGCGGT TCCGCCTGTG CGCCGGCCGG   1980
GATCACCACA ATATTCATAG AAAGCTGTCT TGCACCTACC GTATCGCGGG AGATACCGAC   2040
AAAATAGGGC AGTTTTTGCG TGGTATCCGT GGGGTGTTCC GGCCTGACAA TCTTGAGTTG   2100
GTTCGTCATC ATCTTTCTCC ATCTGGGCGA CCTGATCGGT T                      2141
```

The hypersensitive response elicitor polypeptide or protein derived from *Erwinia amylovora* has an amino acid sequence corresponding to SEQ. ID. No. 3 as follows:

```
Met Ser Leu Asn Thr Ser Gly Leu Gly Ala Ser Thr Met Gln Ile Ser
1               5                  10                  15

Ile Gly Gly Ala Gly Gly Asn Asn Gly Leu Leu Gly Thr Ser Arg Gln
            20                  25                  30

Asn Ala Gly Leu Gly Gly Asn Ser Ala Leu Gly Leu Gly Gly Gly Asn
        35                  40                  45

Gln Asn Asp Thr Val Asn Gln Leu Ala Gly Leu Leu Thr Gly Met Met
    50                  55                  60

Met Met Met Ser Met Met Gly Gly Gly Leu Met Gly Gly Gly Leu
65                  70                  75                  80

Gly Gly Gly Leu Gly Asn Gly Leu Gly Gly Ser Gly Gly Leu Gly Glu
            85                  90                  95

Gly Leu Ser Asn Ala Leu Asn Asp Met Leu Gly Gly Ser Leu Asn Thr
            100                 105                 110
```

```
Leu Gly Ser Lys Gly Gly Asn Asn Thr Thr Ser Thr Thr Asn Ser Pro
        115                 120                 125
Leu Asp Gln Ala Leu Gly Ile Asn Ser Thr Ser Gln Asn Asp Asp Ser
        130                 135                 140
Thr Ser Gly Thr Asp Ser Thr Ser Asp Ser Ser Asp Pro Met Gln Gln
145                 150                 155                 160
Leu Leu Lys Met Phe Ser Glu Ile Met Gln Ser Leu Phe Gly Asp Gly
                165                 170                 175
Gln Asp Gly Thr Gln Gly Ser Ser Ser Gly Gly Lys Gln Pro Thr Glu
        180                 185                 190
Gly Glu Gln Asn Ala Tyr Lys Lys Gly Val Thr Asp Ala Leu Ser Gly
        195                 200                 205
Leu Met Gly Asn Gly Leu Ser Gln Leu Leu Gly Asn Gly Gly Leu Gly
        210                 215                 220
Gly Gly Gln Gly Gly Asn Ala Gly Thr Gly Leu Asp Gly Ser Ser Leu
225                 230                 235                 240
Gly Gly Lys Gly Leu Gln Asn Leu Ser Gly Pro Val Asp Tyr Gln Gln
                245                 250                 255
Leu Gly Asn Ala Val Gly Thr Gly Ile Gly Met Lys Ala Gly Ile Gln
                260                 265                 270
Ala Leu Asn Asp Ile Gly Thr His Arg His Ser Ser Thr Arg Ser Phe
        275                 280                 285
Val Asn Lys Gly Asp Arg Ala Met Ala Lys Glu Ile Gly Gln Phe Met
        290                 295                 300
Asp Gln Tyr Pro Glu Val Phe Gly Lys Pro Gln Tyr Gln Lys Gly Pro
305                 310                 315                 320
Gly Gln Glu Val Lys Thr Asp Asp Lys Ser Trp Ala Lys Ala Leu Ser
                325                 330                 335
Lys Pro Asp Asp Asp Gly Met Thr Pro Ala Ser Met Glu Gln Phe Asn
                340                 345                 350
Lys Ala Lys Gly Met Ile Lys Arg Pro Met Ala Gly Asp Thr Gly Asn
        355                 360                 365
Gly Asn Leu Gln Ala Arg Gly Ala Gly Gly Ser Ser Leu Gly Ile Asp
        370                 375                 380
Ala Met Met Ala Gly Asp Ala Ile Asn Asn Met Ala Leu Gly Lys Leu
385                 390                 395                 400
Gly Ala Ala
```

This hypersensitive response elicitor polypeptide or protein has a molecular weight of about 39 kDa, it has a pI of approximately 4.3, and is heat stable at 100° C. for at least 10 minutes. This hypersensitive response elicitor polypeptide or protein has substantially no cysteine. The hypersensitive response elicitor polypeptide or protein derived from Erwinia amylovora is more fully described in Wei, Z.-M., R. J. Laby, C. H. Zumoff, D. W. Bauer, S.-Y. He, A. Collmer, and S. V. Beer, "Harpin, Elicitor of the Hypersensitive Response Produced by the Plant Pathogen Erwinia amylovora," Science 257:85–88 (1992), which is hereby incorporated by reference. The DNA molecule encoding this polypeptide or protein has a nucleotide sequence corresponding to SEQ. ID. No. 4 as follows:

```
AAGCTTCGGC ATGGCACGTT TGACCGTTGG GTCGGCAGGG TACGTTTGAA TTATTCATAA    60
GAGGAATACG TTATGAGTCT GAATACAAGT GGGCTGGGAG CGTCAACGAT GCAAATTTCT   120
ATCGGCGGTG CGGGCGGAAA TAACGGGTTG CTGGGTACCA GTCGCCAGAA TGCTGGGTTG   180
GGTGGCAATT CTGCACTGGG GCTGGGCGGC GGTAATCAAA ATGATACCGT CAATCAGCTG   240
GCTGGCTTAC TCACCGGCAT GATGATGATG ATGAGCATGA TGGGCGGTGG TGGGCTGATG   300
GGCGGTGGCT TAGGCGGTGG CTTAGGTAAT GGCTTGGGTG GCTCAGGTGG CCTGGGCGAA   360
```

-continued

```
GGACTGTCGA ACGCGCTGAA AGATATGTTA GGCGGTTCGC TGAACACGCT GGGCTCGAAA    420

GGCGGCAACA ATACCACTTC AACAACAAAT TCCCCGCTGG ACCAGGCGCT GGGTATTAAC    480

TCAACGTCCC AAAACGACGA TTCCACCTCC GGCACAGATT CCACCTCAGA CTCCAGCGAC    540

CCGATGCAGC AGCTGCTGAA GATGTTCAGC GAGATAATGC AAAGCCTGTT TGGTGATGGG    600

CAAGATGGCA CCCAGGGCAG TTCCTCTGGG GGCAAGCAGC CGACCGAAGG CGAGCAGAAC    660

GCCTATAAAA AAGGAGTCAC TGATGCGCTG TCGGGCCTGA TGGGTAATGG TCTGAGCCAG    720

CTCCTTGGCA ACGGGGGACT GGGAGGTGGT CAGGGCGGTA ATGCTGGCAC GGGTCTTGAC    780

GGTTCGTCGC TGGGCGGCAA AGGGCTGCAA AACCTGAGCG GGCCGGTGGA CTACCAGCAG    840

TTAGGTAACG CCGTGGGTAC CGGTATCGGT ATGAAAGCGG GCATTCAGGC GCTGAATGAT    900

ATCGGTACGC ACAGGCACAG TTCAACCCGT TCTTTCGTCA ATAAAGGCGA TCGGGCGATG    960

GCGAAGGAAA TCGGTCAGTT CATGGACCAG TATCCTGAGG TGTTTGGCAA GCCGCAGTAC   1020

CAGAAAGGCC CGGGTCAGGA GGTGAAAACC GATGACAAAT CATGGGCAAA AGCACTGAGC   1080

AAGCCAGATG ACGACGGAAT GACACCAGCC AGTATGGAGC AGTTCAACAA AGCCAAGGGC   1140

ATGATCAAAA GGCCCATGGC GGGTGATACC GGCAACGGCA ACCTGCAGGC ACGCGGTGCC   1200

GGTGGTTCTT CGCTGGGTAT TGATGCCATG ATGGCCGGTG ATGCCATTAA CAATATGGCA   1260

CTTGGCAAGC TGGGCGCGGC TTAAGCTT                                      1288
```

The hypersensitive response elicitor polypeptide or protein derived from *Pseudomonas syringae* has an amino acid sequence corresponding to SEQ. ID. No. 5 as follows:

```
Met Gln Ser Leu Ser Leu Asn Ser Ser Ser Leu Gln Thr Pro Ala Met
1               5                   10                  15

Ala Leu Val Leu Val Arg Pro Glu Ala Glu Thr Thr Gly Ser Thr Ser
            20                  25                  30

Ser Lys Ala Leu Gln Glu Val Val Val Lys Leu Ala Glu Glu Leu Met
        35                  40                  45

Arg Asn Gly Gln Leu Asp Asp Ser Ser Pro Leu Gly Lys Leu Leu Ala
    50                  55                  60

Lys Ser Met Ala Ala Asp Gly Lys Ala Gly Gly Gly Ile Glu Asp Val
65                  70                  75                  80

Ile Ala Ala Leu Asp Lys Leu Ile His Glu Lys Leu Gly Asp Asn Phe
                85                  90                  95

Gly Ala Ser Ala Asp Ser Ala Ser Gly Thr Gly Gln Gln Asp Leu Met
            100                 105                 110

Thr Gln Val Leu Asn Gly Leu Ala Lys Ser Met Leu Asp Asp Leu Leu
        115                 120                 125

Thr Lys Gln Asp Gly Gly Thr Ser Phe Ser Glu Asp Asp Met Pro Met
    130                 135                 140

Leu Asn Lys Ile Ala Gln Phe Met Asp Asp Asn Pro Ala Gln Phe Pro
145                 150                 155                 160

Lys Pro Asp Ser Gly Ser Trp Val Asn Glu Leu Lys Glu Asp Asn Phe
                165                 170                 175

Leu Asp Gly Asp Glu Thr Ala Ala Phe Arg Ser Ala Leu Asp Ile Ile
            180                 185                 190

Gly Gln Gln Leu Gly Asn Gln Gln Ser Asp Ala Gly Ser Leu Ala Gly
        195                 200                 205
```

-continued

```
Thr Gly Gly Gly Leu Gly Thr Pro Ser Ser Phe Ser Asn Asn Ser Ser
    210                 215                 220

Val Met Gly Asp Pro Leu Ile Asp Ala Asn Thr Gly Pro Gly Asp Ser
225                 230                 235                 240

Gly Asn Thr Arg Gly Glu Ala Gly Gln Leu Ile Gly Glu Leu Ile Asp
                245                 250                 255

Arg Gly Leu Gln Ser Val Leu Ala Gly Gly Leu Gly Thr Pro Val
                260                 265                 270

Asn Thr Pro Gln Thr Gly Thr Ser Ala Asn Gly Gly Gln Ser Ala Gln
            275                 280                 285

Asp Leu Asp Gln Leu Leu Gly Gly Leu Leu Leu Lys Gly Leu Glu Ala
            290                 295                 300

Thr Leu Lys Asp Ala Gly Gln Thr Gly Thr Asp Val Gln Ser Ser Ala
305                 310                 315                 320

Ala Gln Ile Ala Thr Leu Leu Val Ser Thr Leu Leu Gln Gly Thr Arg
                325                 330                 335

Asn Gln Ala Ala Ala
            340
```

This hypersensitive response elicitor polypeptide or protein has a molecular weight of 34–35 kDa. It is rich in glycine (about 13.5%) and lacks cysteine and tyrosine. Further information about the hypersensitive response elicitor derived from *Pseudomonas syringae* is found in He, S. Y., H. C. Huang, and A. Collmer, "*Pseudomonas syringae* pv. syringae Harpin$_{Pss}$: a Protein that is Secreted via the Hrp Pathway and Elicits the Hypersensitive Response in Plants," *Cell* 73:1255–1266 (1993), which is hereby incorporated by reference. The DNA molecule encoding the hypersensitive response elicitor from *Pseudomonas syringae* has a nucleotide sequence corresponding to SEQ. ID. No. 6 as follows:

```
ATGCAGAGTC TCAGTCTTAA CAGCAGCTCG CTGCAAACCC CGGCAATGGC CCTTGTCCTG    60

GTACGTCCTG AAGCCGAGAC GACTGGCAGT ACGTCGAGCA AGGCGCTTCA GGAAGTTGTC   120

GTGAAGCTGG CCGAGGAACT GATGCGCAAT GGTCAACTCG ACGACAGCTC GCCATTGGGA   180

AAACTGTTGG CCAAGTCGAT GGCCGCAGAT GGCAAGGCGG GCGGCGGTAT TGAGGATGTC   240

ATCGCTGCGC TGGACAAGCT GATCCATGAA AAGCTCGGTG ACAACTTCGG CGCGTCTGCG   300

GACAGCGCCT CGGGTACCGG ACAGCAGGAC CTGATGACTC AGGTGCTCAA TGGCCTGGCC   360

AAGTCGATGC TCGATGATCT TCTGACCAAG CAGGATGGCG GGACAAGCTT CTCCGAAGAC   420

GATATGCCGA TGCTGAACAA GATCGCGCAG TTCATGGATG ACAATCCCGC ACAGTTTCCC   480

AAGCCGGACT CGGGCTCCTG GGTGAACGAA CTCAAGGAAG ACAACTTCCT TGATGGCGAC   540

GAAACGGCTG CGTTCCGTTC GGCACTCGAC ATCATTGGCC AGCAACTGGG TAATCAGCAG   600

AGTGACGCTG GCAGTCTGGC AGGGACGGGT GGAGGTCTGG GCACTCCGAG CAGTTTTTCC   660

AACAACTCGT CCGTGATGGG TGATCCGCTG ATCGACGCCA ATACCGGTCC CGGTGACAGC   720

GGCAATACCC GTGGTGAAGC GGGGCAACTG ATCGGCGAGC TTATCGACCG TGGCCTGCAA   780

TCGGTATTGG CCGGTGGTGG ACTGGGCACA CCCGTAAACA CCCCGCAGAC CGGTACGTCG   840

GCGAATGGCG GACAGTCCGC TCAGGATCTT GATCAGTTGC TGGGCGGCTT GCTGCTCAAG   900

GGCCTGGAGG CAACGCTCAA GGATGCCGGG CAAACAGGCA CCGACGTGCA GTCGAGCGCT   960

GCGCAAATCG CCACCTTGCT GGTCAGTACG CTGCTGCAAG GCACCCGCAA TCAGGCTGCA  1020

GCCTGA                                                             1026
```

The hypersensitive response elicitor polypeptide or protein derived from *Pseudomonas solanacearum* has an amino acid sequence corresponding to SEQ. ID. No. 7 as follows:

```
Met Ser Val Gly Asn Ile Gln Ser Pro Ser Asn Leu Pro Gly Leu Gln
1               5                   10                  15

Asn Leu Asn Leu Asn Thr Asn Thr Asn Ser Gln Gln Ser Gly Gln Ser
            20                  25                  30

Val Gln Asp Leu Ile Lys Gln Val Glu Lys Asp Ile Leu Asn Ile Ile
        35                  40                  45

Ala Ala Leu Val Gln Lys Ala Ala Gln Ser Ala Gly Gly Asn Thr Gly
    50                  55                  60

Asn Thr Gly Asn Ala Pro Ala Lys Asp Gly Asn Ala Asn Ala Gly Ala
65                  70                  75                  80

Asn Asp Pro Ser Lys Asn Asp Pro Ser Lys Ser Gln Ala Pro Gln Ser
                85                  90                  95

Ala Asn Lys Thr Gly Asn Val Asp Asp Ala Asn Asn Gln Asp Pro Met
            100                 105                 110

Gln Ala Leu Met Gln Leu Leu Glu Asp Leu Val Lys Leu Leu Lys Ala
        115                 120                 125

Ala Leu His Met Gln Gln Pro Gly Gly Asn Asp Lys Gly Asn Gly Val
    130                 135                 140

Gly Gly Ala Asn Gly Ala Lys Gly Ala Gly Gly Gln Gly Gly Leu Ala
145                 150                 155                 160

Glu Ala Leu Gln Glu Ile Glu Gln Ile Leu Ala Gln Leu Gly Gly Gly
                165                 170                 175

Gly Ala Gly Ala Gly Gly Ala Gly Gly Gly Val Gly Gly Ala Gly Gly
            180                 185                 190

Ala Asp Gly Gly Ser Gly Ala Gly Gly Ala Gly Gly Ala Asn Gly Ala
        195                 200                 205

Asp Gly Gly Asn Gly Val Asn Gly Asn Gln Ala Asn Gly Pro Gln Asn
    210                 215                 220

Ala Gly Asp Val Asn Gly Ala Asn Gly Ala Asp Asp Gly Ser Glu Asp
225                 230                 235                 240

Gln Gly Gly Leu Thr Gly Val Leu Gln Lys Leu Met Lys Ile Leu Asn
                245                 250                 255

Ala Leu Val Gln Met Met Gln Gln Gly Gly Leu Gly Gly Gly Asn Gln
            260                 265                 270

Ala Gln Gly Gly Ser Lys Gly Ala Gly Asn Ala Ser Pro Ala Ser Gly
        275                 280                 285

Ala Asn Pro Gly Ala Asn Gln Pro Gly Ser Ala Asp Asp Gln Ser Ser
    290                 295                 300

Gly Gln Asn Asn Leu Gln Ser Gln Ile Met Asp Val Val Lys Glu Val
305                 310                 315                 320

Val Gln Ile Leu Gln Gln Met Leu Ala Ala Gln Asn Gly Gly Ser Gln
                325                 330                 335

Gln Ser Thr Ser Thr Gln Pro Met
            340
```

It is encoded by a DNA molecule having a nucleotide sequence corresponding SEQ. ID. No. 8 as follows:

```
ATGTCAGTCG GAAACATCCA GAGCCCGTCG AACCTCCCGG GTCTGCAGAA CCTGAACCTC     60

AACACCAACA CCAACAGCCA GCAATCGGGC CAGTCCGTGC AAGACCTGAT CAAGCAGGTC    120
```

-continued

```
GAGAAGGACA TCCTCAACAT CATCGCAGCC CTCGTGCAGA AGGCCGCACA GTCGGCGGGC    180

GGCAACACCG GTAACACCGG CAACGCGCCG GCGAAGGACG GCAATGCCAA CGCGGGCGCC    240

AACGACCCGA GCAAGAACGA CCCGAGCAAG AGCCAGGCTC CGCAGTCGGC CAACAAGACC    300

GGCAACGTCG ACGACGCCAA CAACCAGGAT CCGATGCAAG CGCTGATGCA GCTGCTGGAA    360

GACCTGGTGA AGCTGCTGAA GGCGGCCCTG CACATGCAGC AGCCCGGCGG CAATGACAAG    420

GGCAACGGCG TGGGCGGTGC CAACGGCGCC AAGGGTGCCG GCGGCCAGGG CGGCCTGGCC    480

GAAGCGCTGC AGGAGATCGA GCAGATCCTC GCCCAGCTCG GCGGCGGCGG TGCTGGCGCC    540

GGCGGCGCGG GTGGCGGTGT CGGCGGTGCT GGTGGCGCGG ATGGCGGCTC CGGTGCGGGT    600

GGCGCAGGCG GTGCGAACGG CGCCGACGGC GGCAATGGCG TGAACGGCAA CCAGGCGAAC    660

GGCCCGCAGA ACGCAGGCGA TGTCAACGGT GCCAACGGCG CGGATGACGG CAGCGAAGAC    720

CAGGGCGGCC TCACCGGCGT GCTGCAAAAG CTGATGAAGA TCCTGAACGC GCTGGTGCAG    780

ATGATGCAGC AAGGCGGCCT CGGCGGCGGC AACCAGGCGC AGGGCGGCTC GAAGGGTGCC    840

GGCAACGCCT CGCCGGCTTC CGGCGCGAAC CCGGGCGCGA ACCAGCCCGG TTCGGCGGAT    900

GATCAATCGT CCGGCCAGAA CAATCTGCAA TCCCAGATCA TGGATGTGGT GAAGGAGGTC    960

GTCCAGATCC TGCAGCAGAT GCTGGCGGCG CAGAACGGCG GCAGCCAGCA GTCCACCTCG   1020

ACGCAGCCGA TGTAA                                                    1035
```

Further information regarding the hypersensitive response elicitor polypeptide or protein derived from *Pseudomonas solanacearum* is set forth in Arlat, M., F. Van Gijsegem, J. C. Huet, J. C. Pemollet, and C. A. Boucher, "PopA1, a Protein which Induces a Hypersensitive-like Response in Specific Petunia Genotypes, is Secreted via the Hrp Pathway of *Pseudomonas solanacearum,*" *EMBO J.* 13:543–533 (1994), which is hereby incorporated by reference.

The hypersensitive response elicitor polypeptide or protein from *Xanthomonas campestris* pv. *glycines* has an amino acid sequence corresponding to SEQ. ID. No. 9 as follows:

```
Thr Leu Ile Glu Leu Met Ile Val Val Ala Ile Ile Ala
Ile
1               5                   10
                   15

Ala Ile Leu Ala Ala Ile Ala Leu Pro Ala Tyr Gln
        15                  20

Asp Tyr
25
```

This sequence is an amino terminal sequence having 26 residues only from the hypersensitive response elicitor polypeptide or protein of *Xanthomonas campestris* pv. *glycines*. It matches with fimbrial subunit proteins determined in other *Xanthomonas campestris* pathovars.

The hypersensitive response elicitor polypeptide or protein from *Xanthomonas campestris pelargonii* is heat stable, protease sensitive, and has a molecular weight of 20 kDa. It includes an amino acid sequence corresponding to SEQ. ID. No. 10 as follows:

```
Ser Ser Gln Gln Ser Pro Ser Ala Gly Ser Glu Gln
1               5                   10

Gln Leu Asp Gln Leu Leu Ala Met
        15                  20
```

Isolation of *Erwinia carotovora* hypersensitive response elicitor protein or polypeptide is described in Cai, et al., "The RsmA$^{-}$ Mutants of *Erwinia carotovora* subsp. carotova Strain Ecc71Overexpress hrpN$_{Ecc}$ and Elicit a Hypersensitive Reaction-Like Response in Tobacco Leaves, " *MPMI*, 9(7):565–73 (1996), which is hereby incorporated by reference. The hypersensitive response elicitor protein or polypeptide for *Erwinia stewartii* is disclosed in Ahmad, et al., "Harpin is Not Necessary for the Pathogenicity of *Erwinia stewartii* on Maize," 8*th Int'l. Cong. Molec. Plant-Microbe Interact*, Jul. 14–19, 1996 and Ahmad, et al., "Harpin is Not Necessary for the Pathogenicity of *Erwinia stewartii* on Maize," *Ann. Mtg. Am. Phytopath. Soc*., Jul. 27–31, 1996, which are hereby incorporated by reference.

Hypersensitive response elicitor proteins or polypeptides from *Phytophora parasitica, Phytophora cryptogea, Phytophora cinnamoni, Phytophora capsici, Phytophora megasperma*, and *Phytophora citrophthora* are described in Kamoun, et al., "Extracellular Protein Elicitors from Phytophora: Host-Specificity and Induction of Resistance to Bacterial and Fungal Phytopathogens," *Molec. Plant-Microbe Interact*., 6(1):15–25 (1993), Ricci, et al., "Structure and Activity of Proteins from Pathogenic Fungi Phytophora Eliciting Necrosis and Acquired Resistance in Tobacco," *Eur. J. Biochem*., 183:555–63 (1989), Ricci, et al., "Differential Production of Parasiticein, an Elicitor of Necrosis and Resistance in Tobacco by Isolates of *Phytophora paraticica," Plant Path*., 41:298–307 (1992), Baillieul, et al., "A New Elicitor of the Hypersensitive Response in Tobacco: A Fungal Glycoprotein Elicits Cell Death, Expression of Defense Genes, Production of Salicylic Acid, and Induction of Systemic Acquired Resistance,"

*Plant J.*, 8(4):551–60 (1995), and Bonnet, et al., "Acquired Resistance Triggered by Elicitins in Tobacco and Other Plants," *Eur. J. Plant Path.*, 102:181–92 (1996), which are hereby incorporated by reference.

The above elicitors are exemplary. Other elicitors can be identified by growing fungi or bacteria that elicit a hypersensitive response under which genes encoding an elicitor are expressed. Cell-free preparations from culture supernatants can be tested for elicitor activity (i.e. local necrosis) by using them to infiltrate appropriate plant tissues.

It is also possible to use fragments of the above hypersensitive response elicitor polypeptides or proteins as well as fragments of full length elicitors from other pathogens, in the method of the present invention.

Suitable fragments can be produced by several means. In the first, subclones of the gene encoding a known elicitor protein are produced by conventional molecular genetic manipulation by subcloning gene fragments. The subclones then are expressed in vitro or in vivo in bacterial cells to yield a smaller protein or a peptide that can be tested for elicitor activity according to the procedure described below.

As an alternative, fragments of an elicitor protein can be produced by digestion of a full-length elicitor protein with proteolytic enzymes like chymotrypsin or Staphylococcus proteinase A, or trypsin. Different proteolytic enzymes are likely to cleave elicitor proteins at different sites based on the amino acid sequence of the elicitor protein. Some of the fragments that result from proteolysis may be active elicitors of resistance.

In another approach, based on knowledge of the primary structure of the protein, fragments of the elicitor protein gene may be synthesized by using the PCR technique together with specific sets of primers chosen to represent particular portions of the protein. These then would be cloned into an appropriate vector for increased expression of a truncated peptide or protein.

An example of a suitable fragment is the popA1 fragment of the hypersensitive response elicitor polypeptide or protein from *Pseudomonas solanacearum*. See Arlat, M., F. Van Gijsegem, J. C. Huet, J. C. Pemollet, and C. A. Boucher, "PopA1, a Protein Which Induces a Hypersensitive-like Response in Specific Petunia Genotypes is Secreted via the Hrp Pathway of *Pseudomonas solanacearum*," *EMBO J.* 13:543–53 (1994), which is hereby incorporated by reference. As to *Erwinia amylovora*, a suitable fragment can be, for example, either or both the polypeptide extending between and including amino acids 1 and 98 of SEQ. ID. NO. 3 and the polypeptide extending between and including amino acids 137 and 204 of SEQ. ID. No. 3.

Variants may be made by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide.

The protein or polypeptide of the present invention is preferably produced in purified form (preferably at least about 60%, more preferably 80%, pure) by conventional techniques. Typically, the protein or polypeptide of the present invention is produced but not secreted into the growth medium of recombinant *E. coli*. Alternatively, the protein or polypeptide of the present invention is secreted into the growth medium. In the case of unsecreted protein, to isolate the protein, the *E. coli* host cell carrying a recombinant plasmid is propagated, homogenized, and the homogenate is centrifuged to remove bacterial debris. The supernatant is then subjected to heat treatment and the hypersensitive response elicitor protein is separated by centrifugation. The supernatant fraction containing the polypeptide or protein of the present invention is subjected to gel filtration in an appropriately sized dextran or polyacrylamide column to separate the proteins. If necessary, the protein fraction may be further purified by ion exchange or HPLC.

Alternatively, the hypersensitive response elicitor protein can be prepared by chemical synthesis using conventional techniques.

The DNA molecule encoding the hypersensitive response elicitor polypeptide or protein can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transection of plasmids into cells infected with virus.

Suitable vectors include, but are not limited to, the following viral vectors such as lambda vector system gtll, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif, which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (MRNA) translation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promoters. Furthermore, eucaryotic promotors and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. col*, its bacteriophages, or plasmids, promoters such as the T7 phage promoter, lac promotor, trp promotor, recA promotor, ribosomal RNA promotor, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the hypersensitive response elicitor polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The method of the present invention can be utilized to treat seeds for a wide variety of plants to impart pathogen resistance to the plants. Suitable seeds are for plants which are dicots and monocots. More particularly, useful crop plants can include: rice, wheat, barley, rye, oats, cotton, sunflower, canola, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane. Examples of suitable ornamental plants are: rose, Saintpaulia, petunia, Pelargonium, poinsettia, chrysanthemum, carnation, and zinnia.

The method of imparting pathogen resistance to plants in accordance with the present invention is useful in imparting resistance to a wide variety of pathogens including viruses, bacteria, and fungi.

Resistance, inter alia, to the following viruses can be achieved by the method of the present invention: Tobacco mosaic virus, cucumber mosaic virus, potato x virus, potato y virus, and tomato mosaic virus.

Resistance, inter alia, to the following bacteria can also be imparted to plants in accordance with the present invention: *Pseudomonas solancearum, Pseudomonas syringae* pv. tabaci, and *Xanthamonas campestris* pv. *pelargonii.*

Plants can be made resistant, inter alia, to the following fungi by use of the method of the present invention: *Fusarium oxysporum* and *Phytophthora infestans.*

The embodiment of the present invention involving applying the hypersensitive response elicitor polypeptide or protein to all or part of the plant seeds being treated can be carried out through a variety of procedures. Suitable application methods include high or low pressure spraying, injection, coating, dusting, and immersion. Other suitable application procedures can be envisioned by those skilled in the art. Once treated with the hypersensitive response elicitor of the present invention, the seeds can be planted and cultivated using conventional procedures to produce plants. After plants have been propagated from seeds treated in accordance with the present invention, the plants may be treated with one or more applications of the hypersensitive response elicitor protein or polypeptide to enhance hypersensitive response induced resistance in the plants. See U.S. patent application Ser. No. 08/475,775, which is hereby incorporated by reference. Such propagated plants, which are resistant to disease, may, in turn, be useful in producing seeds or propagules (e.g. cuttings) that produce resistant plants.

The hypersensitive response elicitor polypeptide or protein can be applied to plant seeds in accordance with the present invention alone or in a mixture with other materials.

A composition suitable for treating plant seeds in accordance with the present invention contains a hypersensitive response elicitor polypeptide or protein in a carrier. Suitable carriers include water, aqueous solutions, slurries, or dry powders. In this embodiment, the composition contains greater than 0.5 nM hypersensitive response elicitor polypeptide or protein.

Although not required, this composition may contain additional additives including fertilizer, insecticide, fungicide, nematicide, herbicide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and abrading agents. These materials can be used to facilitate the process of the present invention. In addition, the hypersensitive response elicitor polypeptide or protein can be applied to plant seeds with other conventional seed formulation and treatment materials, including clays and polysaccharides.

In the alternative embodiment of the present invention involving the use of transgenic seeds, a hypersensitive response elicitor polypeptide or protein need not be applied topically to the seeds. Instead, transgenic plants transformed with a DNA molecule encoding a hypersensitive response elicitor polypeptide or protein are produced according to procedures well known in the art, such as biolistics or Agrobacterium mediated transformation. Examples of suitable hypersensitive response elicitor polypeptides or proteins and the nucleic acid sequences for their encoding DNA are disclosed supra. As is conventional in the art, such transgenic plants would contain suitable vectors with various promoters including pathogen-induced promoters, and other components needed for transformation, transcription, and, possibly, translation. Such transgenic plants themselves could be grown under conditions effective to be imparted with pathogen resistance. In any event, once transgenic plants of this type are produced, transgenic seeds are recovered. These seeds can then be planted in the soil and cultivated using conventional procedures to produce plants. The plants are propagated from the planted transgenic seeds under conditions effective to impart pathogen resistance to the plants.

When transgenic plant seeds are used in accordance with the present invention, they additionally can be treated with the same materials (noted above) as are used to treat the seeds to which a hypersensitive response elicitor polypeptide or protein is applied. These other materials, including hypersensitive response elicitors, can be applied to the transgenic plant seeds by high or low pressure spraying, injection, coating, dusting, and immersion. Similarly, transgenic plants additionally may be treated with one or more applications of the hypersensitive response elicitor to enhance hypersensitive response induced resistance in the plants. Such plants may also be treated with conventional plant treatment agents (e.g., insecticides, fertilizers, etc.). The transgenic plants of the present invention are useful in producing seeds or propagules (e.g. cuttings) from which disease resistant plants grow.

EXAMPLES

Example 1

Effect of Treating Seeds with Hypersensitive Response Elicitor Protein

Marglobe tomato seeds were submerged in hypersensitive response elicitor protein (ca. 26 μgm/ml) from *Erwinia amylovora* solution or buffer in beakers on day 0 for 24 hours at 28° C. in a growth chamber. After soaking seeds in hypersensitive response elicitor protein from *Erwinia amylovora* or buffer, they were sown in germination pots with artificial soil on day 1. Seedlings were transplanted to individual pots at the two-true-leaf stage on day 12. After transplanting, some plants that arose from treated seed also were sprayed with hypersensitive response elicitor protein (ca. 13 μgm/ml) from *Erwinia amylovora* (Treatments 3 and 4).

Tomato treated as noted in the preceding paragraph were inoculated with *Burkholderia* (*Pseudomonas*) *solanacearum* K60 strain (See Kelman, "The Relationship of Pathogenicity in *Pseudomonas solanacearum* to Colony Appearance on a Tetrazolium Medium," *Phytopathology* 44:693–95 (1954)) on day 23 by making vertical cuts through the roots and potting medium of tomato plants (on a tangent 2 cm from the stem and 2 times/pot) and putting 10 ml ($5\times10^8$cfu/ml) suspension into the soil.

The above procedure involved use of 10 seeds treated with hypersensitive response elicitor protein from *Erwinia amylovora* per treatment.

Treatments:

1. Seeds soaked in hypersensitive response elicitor protein from *Erwinia amylovora* (ca. 26 μmg/ml).
2. Seeds soaked in buffer (5 mM $KPO_4$, pH 6.8).
3. Seeds soaked in hypersensitive response elicitor protein from *Erwinia amylovora* (ca. 26 μmg/ml) and seedlings sprayed with hypersensitive response elicitor protein from *Erwinia amylovora* (ca. 13 μgm/ml) at transplanting.
4. Seeds soaked in buffer and seedlings sprayed with hypersensitive response elicitor protein from *Erwinia amylovora* (ca. 13 μgm/ml) at transplanting.

The results of these treatments are set forth in Tables 1–4.

TABLE 1

Infection Data - 28 Days After Seed Treatment and 5 Days After Inoculation

| | | Number of Plants of Given Disease Rating* | | | | | |
|---|---|---|---|---|---|---|---|
| Treatm. | Plants | 0 | 1 | 2 | 3 | 4 | 5 |
| 1 | 10 | 10 | 0 | 0 | 0 | 0 | 0 |
| 2 | 10 | 9 | 1 | 0 | 0 | 0 | 0 |
| 3 | 10 | 9 | 1 | 0 | 0 | 0 | 0 |
| 4 | 10 | 10 | 0 | 0 | 0 | 0 | 0 |

*Disease Scale:
Grade 0: No symptoms
Grade 1: One leaf partially wilted.
Grade 2: 2–3 leaves wilted.
Grade 3: All except the top 2–3 leaves wilted.
Grade 4: All leaves wilted.
Grade 5: Plant Dead

TABLE 2

Infection Data - 31 Days After Seed Treatment and 8 Days After Inoculation

| | | Number of Plants of Given Disease Rating* | | | | | |
|---|---|---|---|---|---|---|---|
| Treatm. | Plants | 0 | 1 | 2 | 3 | 4 | 5 |
| 1 | 10 | 6 | 4 | 0 | 0 | 0 | 0 |
| 2 | 10 | 4 | 3 | 2 | 1 | 0 | 0 |
| 3 | 10 | 8 | 2 | 0 | 0 | 0 | 0 |
| 4 | 10 | 7 | 2 | 1 | 0 | 0 | 0 |

TABLE 3

Infection Data - 35 Days After Seed
Treatment and 12 Days After Inoculation

| Treatm. | Plants | Number of Plants of Given Disease Rating* | | | | | |
|---|---|---|---|---|---|---|---|
| | | 0 | 1 | 2 | 3 | 4 | 5 |
| 1 | 10 | 5 | 3 | 0 | 1 | 1 | 0 |
| 2 | 10 | 1 | 3 | 3 | 2 | 1 | 0 |
| 3 | 10 | 4 | 3 | 3 | 0 | 0 | 0 |
| 4 | 10 | 3 | 3 | 3 | 1 | 0 | 0 |

TABLE 4

Disease Indices of Seed Treatment
With Hypersensitive Response Elicitor Protein

| Treatment | | Inoculation | Disease Index (%)* | | |
|---|---|---|---|---|---|
| Day 0 | Day 14 | Day 23 | Day 28 | Day 31 | Day 35 |
| 1. Hypersensitive response elicitor protein seed soak | | Inoculate | 0 | 8 | 20 |
| 2. Buffer seed soak | | Inoculate | 2 | 20 | 38 |
| 3. Hypersensitive response elicitor protein seed soak | Spray Hypersensitive response elicitor protein | Inoculate | 2 | 4 | 18 |
| 4. Buffer seed soak | Spray Hypersensitive response elicitor protein | Inoculate | 0 | 8 | 24 |

*The Disease Index was determined using the procedure set forth in N.N. Winstead, et al., "Inoculation Techniques for Evaluating Resistance to Pseudomonas Solanacearum," Phytopathology 42:628-34 (1952), particularly at page 629.

The above data shows that the hypersensitive response elicitor protein was more effective than buffer as a seed treatment in reducing disease index and was as effective as spraying leaves of young plants with hypersensitive response elicitor protein.

Example 2

Effect of Treating Tomato Seeds With
Hypersensitive Response Elicitor Protein From
pCPP2139 Versus pCPP50 Vector On Southern
Bacteria Wilt Of Tomato Marglobe tomato seeds were submerged in hypersensitive response elicitor protein from pCPP2139 or in pCPP50 vector solution (1:50, 1:100 and 1:200) in beakers on day 0 for 24 hours at 28° C. in a growth chamber. After soaking seeds in hypersensitive response elicitor protein or vector, they were sown in germination pots with artificial soil on day 0. Ten uniform appearing plants were chosen randomly from each of the following treatments:

| Treatment Content | Strain | Dilution | Harpin |
|---|---|---|---|
| 1. | DH5α(pCPP2139) | 1:50 | 8 µg/ml |
| 2. | DH5α(pCCP50) | 1:50 | 0 |
| 3. | DH5α(pCPP2139) | 1:100 | 4 µg/ml |
| 4. | DH5α(pCPP50) | 1:100 | 0 |
| 5. | DH5α(pCPP2139) | 1:200 | 2 µg/ml |
| 6. | DH5α(pCPP50) | 1:200 | 0 |

The resulting seedlings were inoculated with *Pseudomonas solanacearum* K60 by dipping the roots of tomato seedling plants for about 30 seconds in a 40 ml (1×10$^8$ cfu/ml) suspension. The seedlings were then transplanted into the pots with artificial soil on day 12.

The results of these treatments are set forth in Tables 5–8.

TABLE 5

16 Days After Seed Treatment and
3 Days After Inoculation

| Treatm. | Plants | Number of Plants of Given Disease Rating* | | | | | |
|---|---|---|---|---|---|---|---|
| | | 0 | 1 | 2 | 3 | 4 | 5 |
| 1 | 10 | 7 | 3 | 0 | 0 | 0 | 0 |
| 2 | 10 | 5 | 5 | 0 | 0 | 0 | 0 |
| 3 | 10 | 6 | 4 | 0 | 0 | 0 | 0 |
| 4 | 10 | 6 | 4 | 0 | 0 | 0 | 0 |
| 5 | 10 | 7 | 4 | 0 | 0 | 0 | 0 |
| 6 | 10 | 4 | 6 | 0 | 0 | 0 | 0 |

TABLE 6

19 Days After Seed Treatment and
6 Days After Inoculation

| Treatm. | Plants | Number of Plants of Given Disease Rating* | | | | | |
|---|---|---|---|---|---|---|---|
| | | 0 | 1 | 2 | 3 | 4 | 5 |
| 1 | 10 | 6 | 0 | 0 | 0 | 0 | 0 |
| 2 | 10 | 2 | 0 | 2 | 2 | 1 | 3 |
| 3 | 10 | 2 | 0 | 2 | 0 | 2 | 4 |
| 4 | 10 | 3 | 1 | 2 | 0 | 2 | 2 |
| 5 | 10 | 2 | 1 | 0 | 2 | 2 | 3 |
| 6 | 10 | 1 | 0 | 1 | 1 | 3 | 4 |

TABLE 7

21 Days After Seed Treatment and
8 Days After Inoculation

| Treatm. | Plants | Number of Plants of Given Disease Rating* | | | | | |
|---|---|---|---|---|---|---|---|
| | | 0 | 1 | 2 | 3 | 4 | 5 |
| 1 | 10 | 6 | 0 | 0 | 0 | 1 | 3 |
| 2 | 10 | 2 | 0 | 0 | 1 | 3 | 4 |
| 3 | 10 | 2 | 0 | 0 | 2 | 2 | 3 |
| 4 | 10 | 3 | 0 | 0 | 2 | 2 | 3 |
| 5 | 10 | 2 | 0 | 0 | 0 | 4 | 4 |
| 6 | 10 | 1 | 0 | 1 | 2 | 1 | 5 |

TABLE 8

Disease Indices of Seed Treatment
With Hypersensitive Response Elicitor and Vector

| Treatment | | Disease Index (%) | | |
|---|---|---|---|---|
| Day 0 | Day 12 | Day 15 | Day 18 | Day 20 |
| Hypersensitive response elicitor protein seed dip (1:50) | inoculate | 6.0 | 32.0 | 38.0 |
| Vector seed dip (1:50) | inoculate | 10.0 | 58.0 | 70.0 |
| Hypersensitive response elicitor protein seed dip (1:100) | inoculate | 8.0 | 64.0 | 68.0 |
| Vector seed dip (1:100) | inoculate | 8.0 | 46.0 | 58.0 |
| Hypersensitive response elicitor protein seed dip (1:200) | inoculate | 6.0 | 60.00 | 72.0 |
| Vector seed dip (1:200) | inoculate | 12.0 | 74.0 | 74.0 |

The above data shows that the hypersensitive response elicitor protein is much more effective than the vector solution in preventing Tomato Southern Bacteria Wilt.

Example 3

Effect of Treating Tomato Seeds With Hypersensitive Response Elicitor Protein From pCPP2139 Versus pCPP50 Vector On Tomato Southern Bacteria Wilt Marglobe tomato seeds were submerged in hypersensitive response elicitor protein from pCPP2139 or in pCPP50 vector solution (1:50, 1:100 and 1:200) in beakers on day 0 for 24 hours at 28° C. in a growth chamber. After soaking seeds in the hypersensitive response elicitor protein or vector, the seeds were sown in germination pots with artificial soil on day 1. Ten uniform appearing plants were chosen randomly from each of the following treatments:

| Treatment | Strain | Dilution | Hypersensitive Response Elicitor Content |
|---|---|---|---|
| 1. | DH5α(pCPP2139) | 1:50 | 8 μg/ml |
| 2. | DH5α(pCCP50) | 1:50 | 0 |
| 3. | DH5α(pCPP2139) | 1:100 | 4 μg/ml |
| 4. | DH5α(pCPP50) | 1:100 | 0 |
| 5. | DH5α(pCPP2139) | 1:200 | 2 μg/ml |
| 6. | DH5α(pCPP50) | 1:200 | 0 |

The resulting seedlings were inoculated with *Pseudomonas solanacearum* K60 by dipping the roots of tomato seedling plants for about 30 seconds in a 40 ml ($1\times10^6$ cfu/ml) suspension. The seedlings were then transplanted into the pots with artificial soil on day 12.

The results of these treatments are set forth in Tables 9–12.

TABLE 9

16 Days After Seed Treatment and
3 Days After Inoculation

| | | Number of Plants of Given Disease Rating* | | | | | |
|---|---|---|---|---|---|---|---|
| Treatm. | Plants | 0 | 1 | 2 | 3 | 4 | 5 |
| 1 | 10 | 8 | 2 | 0 | 0 | 0 | 0 |
| 2 | 10 | 7 | 3 | 0 | 0 | 0 | 0 |
| 3 | 10 | 7 | 3 | 0 | 0 | 0 | 0 |
| 4 | 10 | 7 | 3 | 0 | 0 | 0 | 0 |
| 5 | 10 | 8 | 2 | 0 | 0 | 0 | 0 |
| 6 | 10 | 7 | 3 | 0 | 0 | 0 | 0 |

TABLE 10

19 Days After Seed Treatment and
6 Days After Inoculation

| | | Number of Plants of Given Disease Rating* | | | | | |
|---|---|---|---|---|---|---|---|
| Treatm. | Plants | 0 | 1 | 2 | 3 | 4 | 5 |
| 1 | 10 | 5 | 0 | 0 | 1 | 2 | 2 |
| 2 | 10 | 1 | 0 | 1 | 2 | 3 | 3 |
| 3 | 10 | 4 | 1 | 0 | 0 | 2 | 3 |
| 4 | 10 | 2 | 0 | 2 | 1 | 2 | 3 |
| 5 | 10 | 1 | 0 | 1 | 1 | 4 | 3 |
| 6 | 10 | 1 | 0 | 0 | 2 | 4 | 3 |

TABLE 11

21 Days After Hypersensitive Response
Elicitor Protein Seed Treatment and
8 Days After Inoculation

| | | Number of Plants of Given Disease Rating* | | | | | |
|---|---|---|---|---|---|---|---|
| Treatm. | Plants | 0 | 1 | 2 | 3 | 4 | 5 |
| 1 | 10 | 5 | 0 | 0 | 0 | 2 | 3 |
| 2 | 10 | 2 | 0 | 2 | 0 | 2 | 4 |
| 3 | 10 | 5 | 0 | 0 | 0 | 2 | 3 |
| 4 | 10 | 2 | 0 | 2 | 0 | 2 | 4 |
| 5 | 10 | 1 | 0 | 1 | 0 | 2 | 6 |
| 6 | 10 | 1 | 0 | 0 | 0 | 2 | 7 |

TABLE 12

Disease Indices of Seed Treatment
With Hypersensitive Response Elicitor Protein and Vector

| Day 1 | | Day 13 | Day 16 | Day 19 | Day 21 |
|---|---|---|---|---|---|
| Hypersensitive response elicitor protein seed dip (1:50) | inoculate | | 4.0 | 42.0 | 46.0 |
| Vector seed dip (1:50) | inoculate | | 6.0 | 70.0 | 64.0 |
| Hypersensitive response elicitor protein seed dip (1:100) | inoculate | | 6.0 | 48.0 | 46.0 |
| Vector seed dip (1:100) | inoculate | | 6.0 | 60.0 | 64.0 |

TABLE 12-continued

Disease Indices of Seed Treatment With Hypersensitive Response Elicitor Protein and Vector

| Day 1 | Day 13 | Day 16 | Day 19 | Day 21 |
|---|---|---|---|---|
| Hypersensitive response elicitor protein seed dip (1:200) | inoculate | 4.0 | 72.0 | 80.0 |
| Vector seed dip (1:200) | inoculate | 6.0 | 74.0 | 86.0 |

The above data shows that the hypersensitive response elicitor protein is much more effective in preventing Tomato Southern Bacteria Wilt.

Example 4

Effect of Treating Tomato Seeds With Hypersensitive Response Elicitor Protein From pCPP2139 Versus pCPP50 Vector On Southern Bacteria Wilt Of Tomato Marglobe tomato seeds were submerged in hypersensitive response elicitor protein from pCPP2139 or in pCPP50 vector solution (1:25, 1:50 and 1:100) in beakers on day 0 for 24 hours at 28° C. in a growth chamber. After soaking seeds in hypersensitive response elicitor protein or vector, they were sown in germination pots with artificial soil on day 1. Ten uniform appearing plants were chosen randomly from each of the following treatments:

| Treatment Content | Strain | Dilution | Harpin |
|---|---|---|---|
| 1. | DH5α(pCPP2139) | 1:25 | 16 μg/ml |
| 2. | DH5α(pCCP50) | 1:25 | 0 |
| 3. | DH5α(pCPP2139) | 1:50 | 8 μg/ml |
| 4. | DH5α(pCPP50) | 1:50 | 0 |
| 5. | DH5α(pCPP2139) | 1:100 | 2 μg/ml |
| 6. | DH5α(pCPP50) | 1:100 | 0 |

The resulting seedlings were inoculated with *Pseudomonas solanacearum* K60 by dipping the roots of tomato seedling plants for about 30 seconds in a 40 ml ($1 \times 10^8$ cfu/ml) suspension. The seedlings were then transplanted into the pots with artificial soil on day 14.

The results of these treatments are set forth in Tables 13–16.

TABLE 13

19 Days After Seed Treatment and 4 Days After Inoculation

| Treatm. | Plants | Number of Plants of Given Disease Rating* | | | | | |
|---|---|---|---|---|---|---|---|
| | | 0 | 1 | 2 | 3 | 4 | 5 |
| 1 | 10 | 8 | 2 | 0 | 0 | 0 | 0 |
| 2 | 10 | 5 | 2 | 2 | 1 | 0 | 0 |
| 3 | 10 | 9 | 1 | 0 | 0 | 0 | 0 |
| 4 | 10 | 5 | 2 | 1 | 2 | 0 | 0 |
| 5 | 10 | 5 | 3 | 1 | 1 | 0 | 0 |
| 6 | 10 | 6 | 1 | 2 | 1 | 0 | 0 |

TABLE 14

21 Days After Seed Treatments and 6 Days After Inoculation

| Treatm. | Plants | Number of Plants of Given Disease Rating* | | | | | |
|---|---|---|---|---|---|---|---|
| | | 0 | 1 | 2 | 3 | 4 | 5 |
| 1 | 10 | 6 | 3 | 0 | 0 | 1 | 0 |
| 2 | 10 | 3 | 2 | 1 | 0 | 0 | 0 |
| 3 | 10 | 6 | 3 | 1 | 0 | 0 | 0 |
| 4 | 10 | 3 | 2 | 1 | 2 | 2 | 0 |
| 5 | 10 | 5 | 1 | 2 | 2 | 0 | 0 |
| 6 | 10 | 3 | 1 | 3 | 2 | 1 | 0 |

TABLE 15

23 Days After Seed Treatment and 8 Days After Inoculation

| Treatm. | Plants | Number of Plants of Given Disease Rating* | | | | | |
|---|---|---|---|---|---|---|---|
| | | 0 | 1 | 2 | 3 | 4 | 5 |
| 1 | 10 | 7 | 2 | 0 | 0 | 0 | 1 |
| 2 | 10 | 2 | 2 | 2 | 3 | 0 | 1 |
| 3 | 10 | 7 | 2 | 0 | 1 | 0 | 0 |
| 4 | 10 | 2 | 1 | 2 | 3 | 0 | 2 |
| 5 | 10 | 3 | 1 | 2 | 3 | 0 | 1 |
| 6 | 10 | 2 | 2 | 2 | 3 | 0 | 1 |

TABLE 16

Disease Indices of Seed Treatment With Hypersensitive Elicitor Protein and Vector

| Treatment | Disease Index (%) | | | | |
|---|---|---|---|---|---|
| Day 1 | Day 15 | Day 19 | Day 21 | Day 23 | |
| Hypersensitive response elicitor protein seed dip (1:25) | inoculate | 4.0 | 14.0 | 14.0 | |
| Vector seed dip (1:25) | inoculate | 18.0 | 28.0 | 40.0 | |
| Hypersensitive response elicitor protein seed dip (1:50) | inoculate | 2.0 | 10.0 | 10.0 | |
| Vector seed dip (1:50) | inoculate | 20.0 | 36.0 | 48.0 | |
| Hypersensitive response elicitor protein seed dip (1:100) | inoculate | 16.0 | 22.0 | 38.0 | |
| Vector seed dip (1:100) | inoculate | 16.0 | 34.0 | 40.0 | |

The above data shows that the hypersensitive response elicitor protein is much more effective than the vector solution in preventing Tomato Southern Bacteria Wilt. A hypersensitive response protein concentration of 1:50 is particularly effective in disease control.

Example 5

Effect of Treating Tomato Seeds With Hypersensitive Response Elicitor Protein From pCPP2139 Versus pCPP50 Vector On Southern Bacteria Wilt Of Tomato Marglobe tomato seeds were submerged in hypersensitive response elicitor protein from pCPP2139 or pCPP50 vector solution (1:25, 1:50 and 1:100) in beakers on day 0 for 24 hours at 28° C. in a growth chamber. After soaking seeds in hypersensitive response elicitor protein or vector, they were sown in germination pots with artificial soil on day 1. Ten uniform appearing plants were chosen randomly from each of the following treatments:

| Treatment Content | Strain | Dilution | Harpin |
|---|---|---|---|
| 1. | DH5α(pCPP2139) | 1:25 | 16 μg/ml |
| 2. | DH5α(pCCP50) | 1:25 | 0 |
| 3. | DH5α(pCPP2139) | 1:50 | 8 μg/ml |
| 4. | DH5α(pCPP50) | 1:50 | 0 |
| 5. | DH5α(pCPP2139) | 1:100 | 4 μg/ml |
| 6. | DH5α(pCPP50) | 1:100 | 0 |

The resulting seedlings were inoculated with *Pseudomonas solanacearum* K60 by dipping the roots of tomato seedling plants for about 30 seconds in a 40 ml ($1 \times 10^6$ cfu/ml) suspension. The seedlings were then transplanted into the pots with artificial soil on day 14.

The results of these treatments are set forth in Tables 17–20.

TABLE 17

19 Days After Seed Treatment and 4 Days After Inoculation

| Treatm. | Plants | Number of Plants of Given Disease Rating* | | | | | |
|---|---|---|---|---|---|---|---|
| | | 0 | 1 | 2 | 3 | 4 | 5 |
| 1 | 10 | 8 | 2 | 0 | 0 | 0 | 0 |
| 2 | 10 | 6 | 3 | 1 | 0 | 0 | 0 |
| 3 | 10 | 9 | 1 | 0 | 0 | 0 | 0 |
| 4 | 10 | 6 | 4 | 0 | 0 | 0 | 0 |
| 5 | 10 | 6 | 2 | 1 | 1 | 0 | 0 |
| 6 | 10 | 6 | 4 | 0 | 0 | 0 | 0 |

TABLE 18

21 Days After Seed Treatment and 6 Days After Inoculation

| Treatm. | Plants | Number of Plants of Given Disease Rating* | | | | | |
|---|---|---|---|---|---|---|---|
| | | 0 | 1 | 2 | 3 | 4 | 5 |
| 1 | 10 | 7 | 1 | 1 | 1 | 0 | 0 |
| 2 | 10 | 3 | 3 | 2 | 2 | 0 | 0 |
| 3 | 10 | 8 | 2 | 0 | 0 | 0 | 0 |
| 4 | 10 | 3 | 3 | 2 | 2 | 0 | 0 |
| 5 | 10 | 6 | 1 | 1 | 2 | 0 | 0 |
| 6 | 10 | 3 | 2 | 3 | 1 | 1 | 0 |

TABLE 19

23 Days After Seed Treatment and 8 Days After Inoculation

| Treatm. | Plants | Number of Plants of Given Disease Rating* | | | | | |
|---|---|---|---|---|---|---|---|
| | | 0 | 1 | 2 | 3 | 4 | 5 |
| 1 | 10 | 7 | 0 | 2 | 1 | 0 | 0 |
| 2 | 10 | 3 | 1 | 2 | 3 | 0 | 1 |

TABLE 19-continued

23 Days After Seed Treatment and 8 Days After Inoculation

| Treatm. | Plants | Number of Plants of Given Disease Rating* | | | | | |
|---|---|---|---|---|---|---|---|
| | | 0 | 1 | 2 | 3 | 4 | 5 |
| 3 | 10 | 8 | 1 | 0 | 1 | 0 | 0 |
| 4 | 10 | 3 | 3 | 1 | 2 | 0 | 1 |
| 5 | 10 | 3 | 3 | 0 | 2 | 1 | 1 |
| 6 | 10 | 3 | 2 | 0 | 3 | 0 | 2 |

TABLE 20

Disease Indices of Seed Treatment With Hypersensitive Response Elicitor Protein and Vector

| Treatment | | Disease Index (%) | | |
|---|---|---|---|---|
| Day 0 | Day 15 | Day 19 | Day 21 | Day 23 |
| Hypersensitive response elicitor protein seed dip (1:25) | inoculate | 4.0 | 12.0 | 14.0 |
| Vector seed dip (1:25) | inoculate | 10.0 | 26.0 | 38.0 |
| Hypersensitive response elicitor protein seed dip (1:50) | inoculate | 2.0 | 4.0 | 8.0 |
| Vector seed dip (1:50) | inoculate | 8.0 | 26.0 | 32.0 |
| Hypersensitive response elicitor protein seed dip (1:100) | inoculate | 14.0 | 18.0 | 36.0 |
| Vector seed dip (1:100) | inoculate | 8.0 | 30.0 | 42.0 |

The above data shows that the hypersensitive response elicitor protein is much more effective than the vector solution in preventing Tomato Southern Bacteria wilt. A hypersensitive response elicitor protein concentration of 1:50 is more effective in disease control.

Example 6

Treating Rice Seeds with Hypersensitive Response Elicitor Protein to Reduce Rice Stem Rot Rice seeds (variety, M-202) were submerged in two gallons of hypersensitive response elicitor protein solution at a concentration of 20 μpg for 24 hours at room temperature. Rice seeds submerged in the same solution without hypersensitive response elicitor protein were used as a control. After soaking, the seeds were sown in a rice field by air plane spray. There were four replicates for both hypersensitive response elicitor protein and control treatment. The lot size of each replicate is 150 $Ft^2$. The design of each plot was completely randomized, and each plot had substantial level contamination of *Sclerotium oryzae*. Three months after sowing, stem rot was evaluated according to the following rating scale: Scale 1=no disease, 2=disease present on the exterior of the leaf sheath, 3=disease penetrates leaf sheath completely but is not present on culm, 4=disease is present on culm exterior but does not penetrate to interior of culm, and 5=disease penetrates to interior of culm. 40 plants from each replicate were sampled and assessed for the disease incidence and severity. From Table 21, it is apparent that treating seeds with hypersensitive response elicitor reduced both disease incidence and severity. More particularly, regarding incidence, 67% of the plants were infected by stem rot for the control treatment, however, only 40% plants were infected for the hypersensitive response elicitor protein treatment. As to severity, the disease index* for the hypersensitive response elicitor protein treatment was 34% and 60% for the control. accordingly, treating rice seed with hypersensitive response elicitor protein resulted in a significant reduction of stem rot disease. The hypersensitive response elicitor protein-induced resistance in rice can last a season long. In addition to disease resistance, it was also observed that hypersensitive response elicitor protein-treated rice had little or no damage by army worm (*Spodoptera praefica*). In addition, the treated plants were larger and had deeper green color than the control plants.

TABLE 21

Incidence and Severity of Stem Rot
(*Schlerotium oryzae*) on Rice, M-202

| Treatment | % plants given disease rating | | | | | Disease index (%) |
|---|---|---|---|---|---|---|
| | 1 | 2 | 3 | 4 | 5 | (severity) |
| Harpin 20 µg/ml | 60 | 5 | 8 | 18 | 10 | 34 |
| Control | 33 | 5 | 18 | 28 | 18 | 60 |

*Disease Index (%) for the harpin treatment
$$= \frac{1 \times 60 + 2 \times 5 + 3 \times 8 + 4 \times 18 + 5 \times 10}{5 \times 100} \times 100/100$$
*Disease Index (%) for the control treatment
$$= \frac{1 \times 33 + 2 \times 5 + 3 \times 18 + 4 \times 28 + 5 \times 18}{5 \times 100 \times 100/100} \times 100/100$$

Example 7

Effect of Treating Onion Seed with Hypersensitive Response Elicitor Protein on the Development of Onion Smut Disease (*Urocystis cepulae*) and On Seedling Emergence Onion seed, variety Pennant, (Seed Lot# 64387), obtained from the Crookham Co., Caldwell, Id. 83606, treated with hypersensitive response elicitor protein or a control was planted in a natural organic or "muck" soil. Some of the seedlings that grew from the sown seed were healthy, some had lesions characteristic of the Onion Smut disease, and some of the sown seed did not produce seedlings that emerged from the soil. Thus, the effect of treating onion seed with various concentrations of hypersensitive response elicitor protein was determined.

Naturally infested muck soil was obtained from a field in Oswego County, N.Y., where onions had been grown for several years and where the Onion Smut disease commonly had been problematic. Buckets of muck (5-gallon plastic) were stored at 4° C. until used. The soil was mixed, sieved, and put in plastic flats 10 inches wide, 20 inches long, and 2 inches deep for use in the tests described. Based on preliminary experiments, the soil contained many propagules of the Onion Smut fungus, *Urocystis cepulae*, such that when onion seed was sown in the soil, smut lesions developed on many of the seedlings that emerged from the soil. In addition, the soil harbored other microorganisms, including those that cause the "damping-off" disease. Among the several fungi that cause damping off are Pythium, Fusarium, and Rhizoctonia species.

The hypersensitive response elicitor protein encoded by the hrpN gene of *Erwinia amylovora* was used to treat seeds. It was produced by fermentation of the cloned gene in a high-expression vector in *E. coli*. Analysis of the cell-free elicitor preparation by high-pressure liquid chromatography indicated its hypersensitive response elicitor protein content and on that basis appropriate dilutions were prepared in water. Seeds were soaked in a beaker containing hypersensitive response elicitor protein concentrations of 0, 5, 25, and 50 µgm/ml of hypersensitive response elicitor protein for 24 hours. They were removed, dried briefly on paper towels, and sown in the muck soil. Treated seed was arranged by row, 15 seeds in each row for each treatment; each flat contained two replicates, and there were six replicates. Thus, a total of 90 seeds were treated with each concentration of hypersensitive response elicitor protein. The flats containing the seeds were held in a controlled environment chamber operating at 60° F. (15.6° C.), with a 14-hour day /10-hour night. Observations were made on seedling emergence symptoms (smut lesions). The data were recorded 23 days after sowing.

The effect of soaking onion seed in different concentrations of hypersensitive response elicitor protein on emergence of onion seedlings and on the incidence of onion smut is shown in Table 22. Only slight differences in emergence were noted, suggesting that there is no significant effect of treating with hypersensitive response elicitor protein at the concentrations used. Among the seedlings that emerged, substantially more of the seeds that received no hypersensitive response elicitor protein exhibited symptoms of Onion Smut than seedlings that grew from seed that had been treated with hypersensitive response elicitor protein. Treating seed with 25 µgm/ml of hypersensitive response elicitor protein was the most effective concentration tested in reducing Onion Smut. Thus, this example demonstrates that treating onion seed with hypersensitive response elicitor protein reduces the Onion Smut disease.

TABLE 22

Effect of Treating Onion Seed With
Hypersensitive Response Elicitor Protein (i.e. Harpin)
on the Development of Onion Smut Disease
(*Urocystis cepulae*).

| Treatment | Mean Seedlings | Mean | Emerged | |
|---|---|---|---|---|
| harpin (µg/ml) | Emerged (of 15) | Percent Emerged | Percent Healthy | Percent with Smut |
| 0 | 5.00 | 33.3 | 20.0 | 80.0 |
| 5 | 3.67 | 24.4 | 40.9 | 59.1 |
| 25 | 4.33[1] | 28.8 | 50.0 | 46.2 |
| 50 | 4.17 | 27.7 | 44.0 | 56.0 |

[1]One seedling emerged then died.

Example 8

Effect of Treating Tomato Seed with Hypersensitive Response Elicitor Protein on the Development of Bacterial Speck of Tomato (*Pseudomonas syringae* pv. tomato)

Tomato seed, variety New Yorker (Seed lot# 2273–2B), obtained from Harris Seeds, Rochester, N.Y., were treated with four concentrations of hypersensitive response elicitor protein (including a no-elicitor protein, water-treated control) and planted in peatlite soil mix. After 12 days and when the seedlings were in the second true-leaf stage, they were inoculated with the Bacterial Speck pathogen. Ten days later, the treated and inoculated plants were evaluated for extent of infection. Thus, the effect of treating tomato seed with various concentrations of hypersensitive response elicitor protein on resistance to *Pseudomonas syringae* pv. *tomato* was determined.

The hypersensitive response elicitor protein encoded by the hrpN gene of *Rrwinia amylovora* was used to treat seeds. It was produced by fermentation of the cloned gene in a high-expression vector in *E. coli*. Analysis of the cell-free elicitor preparation by high-pressure liquid chromatography indicated its hypersensitive response elicitor protein content and, on that basis, appropriate dilutions were prepared in water. Seeds were soaked in a beaker containing hypersensitive response elicitor protein concentrations of 0, 5, 10, and 20 μgm/ml of hypersensitive response elicitor protein for 24 hours. They were removed, dried briefly on paper towels, and sown. The soil was a mixture of peat and Pearlite™ in plastic flats 10 inches wide, 20 inches long, and 2 inches deep. Treated seed was arranged by row, 6 seeds in each row for each treatment; each flat contained two replicates, and there were four replicates and thus a total of 24 seeds that were treated with each concentration of hypersensitive response elicitor protein. The flats containing the seeds were held in a controlled environment chamber operating at 75° F. (25° C.), with a 14-hour day/10-hour night.

When twelve-days old, the tomato seedlings were inoculated with $10^8$ colony forming units/ml of the pathogen, applied as a foliar spray. The flats containing the seedlings were covered with a plastic dome for 48 hours after inoculation to maintain high humidity. Observations were made on symptom severity using a rating scale of 0–5. The rating was based on the number of lesions that developed on the leaflets and the cotyledons and on the relative damage caused to the plant parts by necrosis that accompanied the lesions. The cotyledons and (true) leaflets were separately rated for disease severity 11 days after inoculation The effect of soaking tomato seed in different concentrations of hypersensitive response elicitor protein (i.e. harpin) on the development of Bacterial Speck on leaflets and cotyledons of tomato is shown in Table 23. The seedlings that grew from seed treated with the highest amount of hypersensitive response elicitor protein tested (20 μgm/ml) had fewer diseased leaflets and cotyledons than the treatments. The water-treated control seedlings did not differ substantially from the plants treated with the two lower concentrations of hypersensitive response elicitor protein. Considering the disease ratings, the results were similar. Only plants treated with the highest concentration of hypersensitive response elicitor protein had disease ratings that were less than those of the other treatments. This example demonsrates that treatment of tomato seed with hypersensitive response elicitor protein reduces the incidence and severity of Bacterial Speck of tomato.

TABLE 23

Effect of Treating Tomato Seed With Hypersensitive Response Elicitor Protein (i.e. Harpin) on the Subsequent Development of Bacterial Speck Disease (*Pseudomonas syringae* pv. tomato) on Tomato Cotyledons and Tomato Leaflets

| | Cotyledons | | | Leaflets | | |
|---|---|---|---|---|---|---|
| Treatment Harpin (μg/ml) | Mean Diseased | Percent Diseased | Disease Rating | Mean Diseased | Percent Diseased | Disease Rating |
| 0 | 6.0/9.0 | 66.6 | 0.8 | 25.8/68.8 | 37.5 | 0.5 |
| 5 | 5.3/7.3 | 72.4 | 0.8 | 22.5/68.0 | 37.5 | 0.5 |
| 10 | 5.8/8.0 | 72.3 | 0.8 | 25.5/66.0 | 38.6 | 0.5 |
| 20 | 5.3/8.5 | 61.8 | 0.6 | 23.8/73.5 | 32.3 | 0.4 |

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of producing plant seeds which impart pathogen resistance to plants grown from the seed, said method comprising:
applying a hypersensitive response elicitor polypeptide or protein in a non-infectious form to plant seeds under conditions effective to impart pathogen resistance to plants grown from the seeds, wherein the hypersynsetive response elicitor is protease sensitive and heat stable at 100° C.

2. A method according to claim 1, wherein the hypersensitive response elicitor polypeptide or protein is in isolated form.

3. A method according to claim 2, wherein the hypersensitive response elicitor polypeptide or protein corresponds to that derived from a pathogen selected from the group consisting of Erwinia, Pseudomonas, Xanthomonas, Phytophthora, and mixtures thereof.

4. A method according to claim 3, wherein the hypersensitive response elicitor polypeptide or protein corresponds to that derived from *Erwinia chrysanthemi*.

5. A method according to claim 3, wherein the hypersensitive response elicitor polypeptide or protein corresponds to that derived from *Erwinia amylovora*.

6. A method according to claim 3, wherein the hypersensitive response elicitor polypeptide or protein corresponds to that derived from *Pseudomonas syringae*.

7. A method according to claim 3, wherein the hypersensitive response elicitor polypeptide or protein corresponds to that derived from *Pseudomonas solanacearum*.

8. A method according to claim 3, wherein the hypersensitive response elicitor polypeptide or protein corresponds to that derived from *Xanthomonas campestris*.

9. A method according to claim 3, wherein the hypersensitive response elicitor polypeptide or protein corresponds to a *Phytophthora species*.

10. A method according to claim 2, wherein the plant is selected from the group consisting of dicots and monocots.

11. A method according to claim 10, wherein the plant is selected from the group consisting of rice, wheat, barley, rye, oats, cotton, sunflower, canola, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

12. A method according to claim 10, wherein the plant is selected from the group consisting of rose, Saintpaulia, petunia, Pelargonium, poinsettia, chrysanthemum, carnation, and zinnia.

13. A method according to claim 2, wherein the pathogen to which the plant is resistant is selected from the group consisting of viruses, bacteria, fungi, and combinations thereof.

14. A method according to claim 2, wherein aid applying is carried out by spraying, injection, oating, dusting or immersion.

15. A method according to claim 2, wherein the hypersensitive response elicitor polypeptide or protein is applied to plant seeds as a composition further comprising a carrier.

16. A method according to claim 15, wherein the carrier is selected from the group consisting of water, aqueous solutions, slurries, and powders.

17. A method according to claim 15, wherein the composition contains greater than 0.5 nM of the hypersensitive response elicitor polypeptide or protein.

18. A method according to claim 15, wherein the composition further contains additives selected from the group consisting of fertilizer, insecticide, nematicide, fungicide, herbicide, and mixtures thereof.

19. A method according to claim 2, wherein said applying causes infiltration of the polypeptide or protein into the plant seed.

20. A method according to claim 2 further comprising:
planting in soil the seeds to which the hypersensitive response elicitor protein or polypeptide has been applied and
propagating plants from the planted seeds.

21. A method according to claim 20 further comprising:
applying the hypersensitive response elicitor polypeptide or protein to the propagated plants to enhance the plant's pathogen resistance.

22. A method according to claim 2, wherein the hypersensitive response elicitor protein or polypeptide is a fungal hypersensitive response elicitor.

23. A pathogen-resistance imparting plant seed to which a non-infectious hypersensitive response elicitor polypeptide or protein has been applied, wherein the application of said non-infectious hypersensitive response elicitor polypeptide or protein imparts pathogen-resistance to a plant grown from said plant seed, wherin the hypersensetive response elicitor is protease sensitive and heat stable at 100° C.

24. A pathogen-resistance imparting plant seed according to claim 23, wherein the hypersensitive response elicitor polypeptide or protein is in isolated form.

25. A pathogen-resistance imparting plant seed according to claim 24, wherein the hypersensitive response elicitor polypeptide or protein corresponds to that derived from a pathogen selected from the group consisting of Erwinia, Pseudomonas, Xanthomonas, Phytophthora, and mixtures thereof.

26. A pathogen-resistance imparting plant seed according to claim 25, wherein the hypersensitive response elicitor polypeptide or protein corresponds to that derived from *Erwinia chrysanthemi*.

27. A pathogen-resistance imparting plant seed according to claim 25, wherein the hypersensitive response elicitor polypeptide or protein corresponds to that derived from *Erwinia amylovora*.

28. A pathogen-resistance imparting plant seed according to claim 25, wherein the hypersensitive response elicitor polypeptide or protein corresponds to that derived from *Pseudomonas syringae*.

29. A pathogen-resistance imparting plant seed according to claim 25, wherein the hypersensitive response elicitor polypeptide or protein corresponds to that derived from *Pseudomonas solanacearum*.

30. A pathogen-resistance imparting plant seed according to claim 25, wherein the hypersensitive response elicitor polypeptide or protein corresponds to that derived from *Xanthomonas campestris*.

31. A pathogen-resistance imparting plant seed according to claim 25, wherein the hypersensitive response polypeptide or protein corresponds to that derived from a Phytophthora species.

32. A pathogen-resistance imparting plant seed according to claim 24, wherein the plant seed is for plants selected from the group consisting of dicots and monocots.

33. A pathogen-resistance imparting plant seed according to claim 32, wherein the plant is selected from the group consisting of rice, wheat, barley, rye, oats, cotton, sunflower, canola, peanut, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

34. A pathogen-resistance imparting plant seed according to claim 32, wherein the plant is selected from the group consisting of rose, Saintpaulia, petunia, Pelangonium, poinsettia, chrysanthemum, carnation, and zinnia.

35. A pathogen-resistance imparting plant seed according to claim 25, wherein the pathogen to which the plant is resistant is selected from the group consisting of a virus, bacterium, fungus, nematode, and combinations thereof.

36. A pathogen-resistance imparting plant seed according to claim 24, wherein the plant seed is infiltrated with the polypeptide or protein.

* * * * *

UNITED STATES PATENT AND TRADEMARK OFFICE
CERTIFICATE OF CORRECTION

PATENT NO. : 6,235,974 B1 Page 1 of 1
DATED : May 22, 2001
INVENTOR(S) : Qui et al.

It is certified that error appears in the above-identified patent and that said Letters Patent is hereby corrected as shown below:

Claim 14,
Line 1, delete "aid" and insert -- said --;
Line 2, delete "oating" and insert -- coating --.

Signed and Sealed this

Twelfth Day of March, 2002

Attest:

Attesting Officer

JAMES E. ROGAN
Director of the United States Patent and Trademark Office

SEQUENCE LISTING

```
(1) GENERAL INFORMATION:

(iii) NUMBER OF SEQUENCES: 10

(2) INFORMATION FOR SEQ ID NO: 1:

(i) SEQUENCE CHARACTERISTICS:
          (A) LENGTH: 338 amino acids
          (B) TYPE: amino acid
          (C) STRANDEDNESS:
          (D) TOPOLOGY: linear (ii) MOLECULE TYPE: protein (xi) SEQUENCE DESCRIPTION: SEQ ID NO: 1:

Met Gln Ile Thr Ile Lys Ala His Ile Gly Gly Asp Leu Gly Val Ser
1               5                   10                  15

Gly Leu Gly Ala Gln Gly Leu Lys Gly Leu Asn Ser Ala Ala Ser Ser
            20                  25                  30

Leu Gly Ser Ser Val Asp Lys Leu Ser Ser Thr Ile Asp Lys Leu Thr
        35                  40                  45

Ser Ala Leu Thr Ser Met Met Phe Gly Gly Ala Leu Ala Gln Gly Leu
```

```
            50                  55                  60
Gly Ala Ser Ser Lys Gly Leu Gly Met Ser Asn Gln Leu Gly Gln Ser
 65                  70                  75                  80

Phe Gly Asn Gly Ala Gln Gly Ala Ser Asn Leu Leu Ser Val Pro Lys
                 85                  90                  95

Ser Gly Gly Asp Ala Leu Ser Lys Met Phe Asp Lys Ala Leu Asp Asp
                100                 105                 110

Leu Leu Gly His Asp Thr Val Thr Lys Leu Thr Asn Gln Ser Asn Gln
                115                 120                 125

Leu Ala Asn Ser Met Leu Asn Ala Ser Gln Met Thr Gln Gly Asn Met
130                 135                 140

Asn Ala Phe Gly Ser Gly Val Asn Asn Ala Leu Ser Ser Ile Leu Gly
145                 150                 155                 160

Asn Gly Leu Gly Gln Ser Met Ser Gly Phe Ser Gln Pro Ser Leu Gly
                165                 170                 175

Ala Gly Gly Leu Gln Gly Leu Ser Gly Ala Gly Ala Phe Asn Gln Leu
                180                 185                 190

Gly Asn Ala Ile Gly Met Gly Val Gly Gln Asn Ala Ala Leu Ser Ala
                195                 200                 205

Leu Ser Asn Val Ser Thr His Val Asp Gly Asn Asn Arg His Phe Val
210                 215                 220

Asp Lys Glu Asp Arg Gly Met Ala Lys Glu Ile Gly Gln Phe Met Asp
225                 230                 235                 240

Gln Tyr Pro Glu Ile Phe Gly Lys Pro Glu Tyr Gln Lys Asp Gly Trp
                245                 250                 255

Ser Ser Pro Lys Thr Asp Asp Lys Ser Trp Ala Lys Ala Leu Ser Lys
                260                 265                 270

Pro Asp Asp Gly Met Thr Gly Ala Ser Met Asp Lys Phe Arg Gln
                275                 280                 285

Ala Met Gly Met Ile Lys Ser Ala Val Ala Gly Asp Thr Gly Asn Thr
290                 295                 300

Asn Leu Asn Leu Arg Gly Ala Gly Gly Ala Ser Leu Gly Ile Asp Ala
305                 310                 315                 320

Ala Val Val Gly Asp Lys Ile Ala Asn Met Ser Leu Gly Lys Leu Ala
                325                 330                 335

Asn Ala (2) INFORMATION FOR SEQ ID NO: 2:

(i) SEQUENCE CHARACTERISTICS:
        (A) LENGTH: 2141 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

CGATTTTACC CGGGTGAACG TGCTATGACC GACAGCATCA CGGTATTCGA CACCGTTACG      60

GCGTTTATGG CCGCGATGAA CCGGCATCAG GCGGCGCGCT GGTCGCCGCA ATCCGGCGTC     120

GATCTGGTAT TTCAGTTTGG GGACACCGGG CGTGAACTCA TGATGCAGAT TCAGCCGGGG     180

CAGCAATATC CCGGCATGTT GCGCACGCTG CTCGCTCGTC GTTATCAGCA GGCGGCAGAG     240

TGCGATGGCT GCCATCTGTG CCTGAACGGC AGCGATGTAT TGATCCTCTG GTGGCCGCTG     300

CCGTCGGATC CCGGCAGTTA TCCGCAGGTG ATCGAACGTT TGTTTGAACT GGCGGGAATG     360
```

-continued

```
ACGTTGCCGT CGCTATCCAT AGCACCGACG GCGCGTCCGC AGACAGGGAA CGGACGCGCC      420
CGATCATTAA GATAAAGGCG GCTTTTTTTA TTGCAAAACG GTAACGGTGA GGAACCGTTT      480
CACCGTCGGC GTCACTCAGT AACAAGTATC CATCATGATG CCTACATCGG GATCGGCGTG      540
GGCATCCGTT GCAGATACTT TTGCGAACAC CTGACATGAA TGAGGAAACG AAATTATGCA      600
AATTACGATC AAAGCGCACA TCGGCGGTGA TTTGGGCGTC TCCGGTCTGG GGCTGGGTGC      660
TCAGGGACTG AAAGGACTGA ATTCCGCGGC TTCATCGCTG GGTTCCAGCG TGGATAAACT      720
GAGCAGCACC ATCGATAAGT TGACCTCCGC GCTGACTTCG ATGATGTTTG GCGGCGCGCT      780
GGCGCAGGGG CTGGGCGCCA GCTCGAAGGG GCTGGGGATG AGCAATCAAC TGGGCCAGTC      840
TTTCGGCAAT GGCGCGCAGG GTGCGAGCAA CCTGCTATCC GTACCGAAAT CCGGCGGCGA      900
TGCGTTGTCA AAAATGTTTG ATAAAGCGCT GGACGATCTG CTGGGTCATG ACACCGTGAC      960
CAAGCTGACT AACCAGAGCA ACCAACTGGC TAATTCAATG CTGAACGCCA GCCAGATGAC      1020
CCAGGGTAAT ATGAATGCGT TCGGCAGCGG TGTGAACAAC GCACTGTCGT CCATTCTCGG      1080
CAACGGTCTC GGCCAGTCGA TGAGTGGCTT CTCTCAGCCT TCTCTGGGGG CAGGCGGCTT      1140
GCAGGGCCTG AGCGGCGCGG GTGCATTCAA CCAGTTGGGT AATGCCATCG GCATGGGCGT      1200
GGGGCAGAAT GCTGCGCTGA GTGCGTTGAG TAACGTCAGC ACCCACGTAG ACGGTAACAA      1260
CCGCCACTTT GTAGATAAAG AAGATCGCGG CATGGCGAAA GAGATCGGCC AGTTTATGGA      1320
TCAGTATCCG GAAATATTCG GTAAACCGGA ATACCAGAAA GATGGCTGGA GTTCGCCGAA      1380
GACGGACGAC AAATCCTGGG CTAAAGCGCT GAGTAAACCG GATGATGACG GTATGACCGG      1440
CGCCAGCATG GACAAATTCC GTCAGGCGAT GGGTATGATC AAAAGCGCGG TGGCGGGTGA      1500
TACCGGCAAT ACCAACCTGA ACCTGCGTGG CGCGGGCGGT GCATCGCTGG GTATCGATGC      1560
GGCTGTCGTC GGCGATAAAA TAGCCAACAT GTCGCTGGGT AAGCTGGCCA ACGCCTGATA      1620
ATCTGTGCTG GCCTGATAAA GCGGAAACGA AAAAGAGAC GGGGAAGCCT GTCTCTTTTC      1680
TTATTATGCG GTTTATGCGG TTACCTGGAC CGGTTAATCA TCGTCATCGA TCTGGTACAA      1740
ACGCACATTT TCCCGTTCAT TCGCGTCGTT ACGCGCCACA ATCGCGATGG CATCTTCCTC      1800
GTCGCTCAGA TTGCGCGGCT GATGGGGAAC GCCGGGTGGA ATATAGAGAA ACTCGCCGGC      1860
CAGATGGAGA CACGTCTGCG ATAAATCTGT GCCGTAACGT GTTTCTATCC GCCCCTTTAG      1920
CAGATAGATT GCGGTTTCGT AATCAACATG GTAATGCGGT TCCGCCTGTG CGCCGGCCGG      1980
GATCACCACA ATATTCATAG AAAGCTGTCT TGCACCTACC GTATCGCGGG AGATACCGAC      2040
AAAATAGGGC AGTTTTTGCG TGGTATCCGT GGGGTGTTCC GGCCTGACAA TCTTGAGTTG      2100
GTTCGTCATC ATCTTTCTCC ATCTGGGCGA CCTGATCGGT T                         2141
```

(2) INFORMATION FOR SEQ ID NO: 3:

(i) SEQUENCE CHARACTERISTICS:
        (A) LENGTH: 403 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 3:

```
Met Ser Leu Asn Thr Ser Gly Leu Gly Ala Ser Thr Met Gln Ile Ser
1               5                   10                  15

Ile Gly Gly Ala Gly Gly Asn Asn Gly Leu Leu Gly Thr Ser Arg Gln
            20                  25                  30
```

```
Asn Ala Gly Leu Gly Gly Asn Ser Ala Leu Gly Leu Gly Gly Asn
            35                  40                  45
Gln Asn Asp Thr Val Asn Gln Leu Ala Gly Leu Leu Thr Gly Met Met
 50                  55                  60
Met Met Met Ser Met Met Gly Gly Gly Leu Met Gly Gly Gly Leu
 65                  70                  75                  80
Gly Gly Gly Leu Gly Asn Gly Leu Gly Ser Gly Gly Leu Gly Glu
                 85                  90                  95
Gly Leu Ser Asn Ala Leu Asn Asp Met Leu Gly Ser Leu Asn Thr
                100                 105                 110
Leu Gly Ser Lys Gly Gly Asn Asn Thr Thr Ser Thr Thr Asn Ser Pro
                115                 120                 125
Leu Asp Gln Ala Leu Gly Ile Asn Ser Thr Ser Gln Asn Asp Asp Ser
                130                 135                 140
Thr Ser Gly Thr Asp Ser Thr Ser Asp Ser Ser Asp Pro Met Gln Gln
145                 150                 155                 160
Leu Leu Lys Met Phe Ser Glu Ile Met Gln Ser Leu Phe Gly Asp Gly
                165                 170                 175
Gln Asp Gly Thr Gln Gly Ser Ser Ser Gly Gly Lys Gln Pro Thr Glu
                180                 185                 190
Gly Glu Gln Asn Ala Tyr Lys Lys Gly Val Thr Asp Ala Leu Ser Gly
                195                 200                 205
Leu Met Gly Asn Gly Leu Ser Gln Leu Leu Gly Asn Gly Gly Leu Gly
                210                 215                 220
Gly Gly Gln Gly Gly Asn Ala Gly Thr Gly Leu Asp Gly Ser Ser Leu
225                 230                 235                 240
Gly Gly Lys Gly Leu Gln Asn Leu Ser Gly Pro Val Asp Tyr Gln Gln
                245                 250                 255
Leu Gly Asn Ala Val Gly Thr Gly Ile Gly Met Lys Ala Gly Ile Gln
                260                 265                 270
Ala Leu Asn Asp Ile Gly Thr His Arg His Ser Ser Thr Arg Ser Phe
                275                 280                 285
Val Asn Lys Gly Asp Arg Ala Met Ala Lys Glu Ile Gly Gln Phe Met
                290                 295                 300
Asp Gln Tyr Pro Glu Val Phe Gly Lys Pro Gln Tyr Gln Lys Gly Pro
305                 310                 315                 320
Gly Gln Glu Val Lys Thr Asp Asp Lys Ser Trp Ala Lys Ala Leu Ser
                325                 330                 335
Lys Pro Asp Asp Gly Met Thr Pro Ala Ser Met Glu Gln Phe Asn
                340                 345                 350
Lys Ala Lys Gly Met Ile Lys Arg Pro Met Ala Gly Asp Thr Gly Asn
                355                 360                 365
Gly Asn Leu Gln Ala Arg Gly Ala Gly Ser Ser Leu Gly Ile Asp
                370                 375                 380
Ala Met Met Ala Gly Asp Ala Ile Asn Asn Met Ala Leu Gly Lys Leu
385                 390                 395                 400
Gly Ala Ala (2) INFORMATION FOR SEQ ID NO: 4:

(i) SEQUENCE CHARACTERISTICS:
        (A) LENGTH: 1288 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO: 4:

```
AAGCTTCGGC ATGGCACGTT TGACCGTTGG GTCGGCAGGG TACGTTTGAA TTATTCATAA      60
GAGGAATACG TTATGAGTCT GAATACAAGT GGGCTGGGAG CGTCAACGAT GCAAATTTCT     120
ATCGGCGGTG CGGGCGGAAA TAACGGGTTG CTGGGTACCA GTCGCCAGAA TGCTGGGTTG     180
GGTGGCAATT CTGCACTGGG GCTGGGCGGC GGTAATCAAA ATGATACCGT CAATCAGCTG     240
GCTGGCTTAC TCACCGGCAT GATGATGATG ATGAGCATGA TGGGCGGTGG TGGGCTGATG     300
GGCGGTGGCT TAGGCGGTGG CTTAGGTAAT GGCTTGGGTG GCTCAGGTGG CCTGGGCGAA     360
GGACTGTCGA ACGCGCTGAA CGATATGTTA GGCGGTTCGC TGAACACGCT GGGCTCGAAA     420
GGCGGCAACA ATACCACTTC AACAACAAAT TCCCCGCTGG ACCAGGCGCT GGGTATTAAC     480
TCAACGTCCC AAAACGACGA TTCCACCTCC GGCACAGATT CCACCTCAGA CTCCAGCGAC     540
CCGATGCAGC AGCTGCTGAA GATGTTCAGC GAGATAATGC AAAGCCTGTT TGGTGATGGG     600
CAAGATGGCA CCCAGGGCAG TTCCTCTGGG GGCAAGCAGC CGACCGAAGG CGAGCAGAAC     660
GCCTATAAAA AAGGAGTCAC TGATGCGCTG TCGGGCCTGA TGGGTAATGG TCTGAGCCAG     720
CTCCTTGGCA ACGGGGACT GGGAGGTGGT CAGGGCGGTA ATGCTGGCAC GGGTCTTGAC      780
GGTTCGTCGC TGGGCGGCAA AGGGCTGCAA AACCTGAGCG GCCGGTGGA CTACCAGCAG      840
TTAGGTAACG CCGTGGGTAC CGGTATCGGT ATGAAAGCGG GCATTCAGGC GCTGAATGAT     900
ATCGGTACGC ACAGGCACAG TTCAACCCGT TCTTTCGTCA ATAAAGGCGA TCGGGCGATG     960
GCGAAGGAAA TCGGTCAGTT CATGGACCAG TATCCTGAGG TGTTTGGCAA GCCGCAGTAC    1020
CAGAAAGGCC CGGGTCAGGA GGTGAAAACC GATGACAAAT CATGGGCAAA AGCACTGAGC    1080
AAGCCAGATG ACGACGGAAT GACACCAGCC AGTATGGAGC AGTTCAACAA AGCCAAGGGC    1140
ATGATCAAAA GGCCCATGGC GGGTGATACC GGCAACGGCA ACCTGCAGGC ACGCGGTGCC    1200
GGTGGTTCTT CGCTGGGTAT TGATGCCATG ATGGCCGGTG ATGCCATTAA CAATATGGCA    1260
CTTGGCAAGC TGGGCGCGGC TTAAGCTT                                       1288
```

(2) INFORMATION FOR SEQ ID NO: 5:

(i) SEQUENCE CHARACTERISTICS:
        (A) LENGTH: 341 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 5:

```
Met Gln Ser Leu Ser Leu Asn Ser Ser Ser Leu Gln Thr Pro Ala Met
  1               5                  10                  15

Ala Leu Val Leu Val Arg Pro Glu Ala Glu Thr Thr Gly Ser Thr Ser
             20                  25                  30

Ser Lys Ala Leu Gln Glu Val Val Lys Leu Ala Glu Glu Leu Met
         35                  40                  45

Arg Asn Gly Gln Leu Asp Asp Ser Ser Pro Leu Gly Lys Leu Leu Ala
     50                  55                  60

Lys Ser Met Ala Ala Asp Gly Lys Ala Gly Gly Ile Glu Asp Val
 65                  70                  75                  80

Ile Ala Ala Leu Asp Lys Leu Ile His Glu Lys Leu Gly Asp Asn Phe
```

```
                      85                  90                  95
Gly Ala Ser Ala Asp Ser Ala Ser Gly Thr Gly Gln Gln Asp Leu Met
               100                 105                 110
Thr Gln Val Leu Asn Gly Leu Ala Lys Ser Met Leu Asp Asp Leu Leu
           115                 120                 125
Thr Lys Gln Asp Gly Gly Thr Ser Phe Ser Glu Asp Asp Met Pro Met
       130                 135                 140
Leu Asn Lys Ile Ala Gln Phe Met Asp Asp Asn Pro Ala Gln Phe Pro
145                 150                 155                 160
Lys Pro Asp Ser Gly Ser Trp Val Asn Glu Leu Lys Glu Asp Asn Phe
               165                 170                 175
Leu Asp Gly Asp Glu Thr Ala Ala Phe Arg Ser Ala Leu Asp Ile Ile
               180                 185                 190
Gly Gln Gln Leu Gly Asn Gln Gln Ser Asp Ala Gly Ser Leu Ala Gly
           195                 200                 205
Thr Gly Gly Leu Gly Thr Pro Ser Ser Phe Ser Asn Asn Ser Ser
       210                 215                 220
Val Met Gly Asp Pro Leu Ile Asp Ala Asn Thr Gly Pro Gly Asp Ser
225                 230                 235                 240
Gly Asn Thr Arg Gly Glu Ala Gly Gln Leu Ile Gly Glu Leu Ile Asp
               245                 250                 255
Arg Gly Leu Gln Ser Val Leu Ala Gly Gly Leu Gly Thr Pro Val
           260                 265                 270
Asn Thr Pro Gln Thr Gly Thr Ser Ala Asn Gly Gly Gln Ser Ala Gln
           275                 280                 285
Asp Leu Asp Gln Leu Leu Gly Gly Leu Leu Lys Gly Leu Glu Ala
       290                 295                 300
Thr Leu Lys Asp Ala Gly Gln Thr Gly Thr Asp Val Gln Ser Ser Ala
305                 310                 315                 320
Ala Gln Ile Ala Thr Leu Leu Val Ser Thr Leu Leu Gln Gly Thr Arg
               325                 330                 335
Asn Gln Ala Ala Ala
           340

(2) INFORMATION FOR SEQ ID NO: 6:

(i) SEQUENCE CHARACTERISTICS:
        (A) LENGTH: 1026 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

ATGCAGAGTC TCAGTCTTAA CAGCAGCTCG CTGCAAACCC CGGCAATGGC CCTTGTCCTG        60

GTACGTCCTG AAGCCGAGAC GACTGGCAGT ACGTCGAGCA AGGCGCTTCA GGAAGTTGTC       120

GTGAAGCTGG CCGAGGAACT GATGCGCAAT GGTCAACTCG ACGACAGCTC GCCATTGGGA       180

AAACTGTTGG CCAAGTCGAT GGCCGCAGAT GGCAAGGCGG GCGGCGGTAT TGAGGATGTC       240

ATCGCTGCGC TGGACAAGCT GATCCATGAA AAGCTCGGTG ACAACTTCGG CGCGTCTGCG       300

GACAGCGCCT CGGGTACCGG ACAGCAGGAC CTGATGACTC AGGTGCTCAA TGGCCTGGCC       360

AAGTCGATGC TCGATGATCT TCTGACCAAG CAGGATGGCG GCACAAGCTT CTCCGAAGAC       420

GATATGCCGA TGCTGAACAA GATCGCGCAG TTCATGGATG ACAATCCCGC ACAGTTTCCC       480
```

```
AAGCCGGACT CGGGCTCCTG GGTGAACGAA CTCAAGGAAG ACAACTTCCT TGATGGCGAC    540

GAAACGGCTG CGTTCCGTTC GGCACTCGAC ATCATTGGCC AGCAACTGGG TAATCAGCAG    600

AGTGACGCTG GCAGTCTGGC AGGGACGGGT GGAGGTCTGG GCACTCCGAG CAGTTTTTCC    660

AACAACTCGT CCGTGATGGG TGATCCGCTG ATCGACGCCA ATACCGGTCC CGGTGACAGC    720

GGCAATACCC GTGGTGAAGC GGGGCAACTG ATCGGCGAGC TTATCGACCG TGGCCTGCAA    780

TCGGTATTGG CCGGTGGTGG ACTGGGCACA CCCGTAAACA CCCCGCAGAC CGGTACGTCG    840

GCGAATGGCG GACAGTCCGC TCAGGATCTT GATCAGTTGC TGGGCGGCTT GCTGCTCAAG    900

GGCCTGGAGG CAACGCTCAA GGATGCCGGG CAAACAGGCA CCGACGTGCA GTCGAGCGCT    960

GCGCAAATCG CCACCTTGCT GGTCAGTACG CTGCTGCAAG GCACCCGCAA TCAGGCTGCA   1020

GCCTGA                                                              1026
```

(2) INFORMATION FOR SEQ ID NO: 7:

(i) SEQUENCE CHARACTERISTICS:
        (A) LENGTH: 344 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 7:

```
Met Ser Val Gly Asn Ile Gln Ser Pro Ser Asn Leu Pro Gly Leu Gln
1               5                   10                  15

Asn Leu Asn Leu Asn Thr Asn Thr Asn Ser Gln Gln Ser Gly Gln Ser
            20                  25                  30

Val Gln Asp Leu Ile Lys Gln Val Glu Lys Asp Ile Leu Asn Ile Ile
        35                  40                  45

Ala Ala Leu Val Gln Lys Ala Ala Gln Ser Ala Gly Gly Asn Thr Gly
    50                  55                  60

Asn Thr Gly Asn Ala Pro Ala Lys Asp Gly Asn Ala Asn Ala Gly Ala
65                  70                  75                  80

Asn Asp Pro Ser Lys Asn Asp Pro Ser Lys Ser Gln Ala Pro Gln Ser
                85                  90                  95

Ala Asn Lys Thr Gly Asn Val Asp Asp Ala Asn Asn Gln Asp Pro Met
            100                 105                 110

Gln Ala Leu Met Gln Leu Leu Glu Asp Leu Val Lys Leu Leu Lys Ala
        115                 120                 125

Ala Leu His Met Gln Gln Pro Gly Gly Asn Asp Lys Gly Asn Gly Val
    130                 135                 140

Gly Gly Ala Asn Gly Ala Lys Gly Ala Gly Gln Gly Gly Leu Ala
145                 150                 155                 160

Glu Ala Leu Gln Glu Ile Glu Gln Ile Leu Ala Gln Leu Gly Gly Gly
            165                 170                 175

Gly Ala Gly Ala Gly Gly Ala Gly Gly Val Gly Gly Ala Gly Gly
        180                 185                 190

Ala Asp Gly Gly Ser Gly Ala Gly Gly Ala Gly Gly Ala Asn Gly Ala
    195                 200                 205

Asp Gly Gly Asn Gly Val Asn Gly Asn Gln Ala Asn Gly Pro Gln Asn
        210                 215                 220

Ala Gly Asp Val Asn Gly Ala Asn Gly Ala Asp Asp Gly Ser Glu Asp
225                 230                 235                 240

Gln Gly Gly Leu Thr Gly Val Leu Gln Lys Leu Met Lys Ile Leu Asn
```

```
                245                 250                 255
Ala Leu Val Gln Met Met Gln Gln Gly Gly Leu Gly Gly Gly Asn Gln
            260                 265                 270
Ala Gln Gly Gly Ser Lys Gly Ala Gly Asn Ala Ser Pro Ala Ser Gly
            275                 280                 285
Ala Asn Pro Gly Ala Asn Gln Pro Gly Ser Ala Asp Asp Gln Ser Ser
            290                 295                 300
Gly Gln Asn Asn Leu Gln Ser Gln Ile Met Asp Val Val Lys Glu Val
305                 310                 315                 320
Val Gln Ile Leu Gln Gln Met Leu Ala Ala Gln Asn Gly Gly Ser Gln
            325                 330                 335
Gln Ser Thr Ser Thr Gln Pro Met
            340
```

(2) INFORMATION FOR SEQ ID NO: 8:

(i) SEQUENCE CHARACTERISTICS:
        (A) LENGTH: 1035 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

```
ATGTCAGTCG GAAACATCCA GAGCCCGTCG AACCTCCCGG GTCTGCAGAA CCTGAACCTC      60
AACACCAACA CCAACAGCCA GCAATCGGGC CAGTCCGTGC AAGACCTGAT CAAGCAGGTC     120
GAGAAGGACA TCCTCAACAT CATCGCAGCC CTCGTGCAGA AGGCCGCACA GTCGGCGGGC     180
GGCAACACCG GTAACACCGG CAACGCGCCG GCGAAGGACG GCAATGCCAA CGCGGGCGCC     240
AACGACCCGA GCAAGAACGA CCCGAGCAAG AGCCAGGCTC CGCAGTCGGC CAACAAGACC     300
GGCAACGTCG ACGACGCCAA CAACCAGGAT CCGATGCAAG CGCTGATGCA GCTGCTGGAA     360
GACCTGGTGA AGCTGCTGAA GCGGCCCCTG CACATGCAGC AGCCCGGCGG CAATGACAAG     420
GGCAACGGCG TGGGCGGTGC CAACGGCGCC AAGGGTGCCG GCGCCAGGG CGGCCTGGCC      480
GAAGCGCTGC AGGAGATCGA GCAGATCCTC GCCCAGCTCG GCGGCGGCGG TGCTGGCGCC     540
GGCGGCGCGG GTGGCGGTGT CGGCGGTGCT GGTGGCGCGG ATGGCGGCTC CGGTGCGGGT     600
GGCGCAGGCG GTGCGAACGG CGCCGACGGC GGCAATGGCG TGAACGGCAA CCAGGCGAAC     660
GGCCCGCAGA ACGCAGGCGA TGTCAACGGT GCCAACGGCG CGGATGACGG CAGCGAAGAC     720
CAGGGCGGCC TCACCGGCGT GCTGCAAAAG CTGATGAAGA TCCTGAACGC GCTGGTGCAG     780
ATGATGCAGC AAGGCGGCCT CGGCGGCGGC AACCAGGCGC AGGGCGGCTC GAAGGGTGCC     840
GGCAACGCCT CGCCGGCTTC CGGCGCGAAC CCGGGCGCGA ACCAGCCCGG TTCGGCGGAT     900
GATCAATCGT CCGGCCAGAA CAATCTGCAA TCCCAGATCA TGGATGTGGT GAAGGAGGTC     960
GTCCAGATCC TGCAGCAGAT GCTGGCGGCG CAGAACGGCG GCAGCCAGCA GTCCACCTCG    1020
ACGCAGCCGA TGTAA                                                    1035
```

(2) INFORMATION FOR SEQ ID NO: 9:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide -continued (xi) SEQUENCE DESCRIPTION: SEQ ID NO: 9:

```
Thr Leu Ile Glu Leu Met Ile Val Val Ala Ile Ile Ala Ile Leu Ala
1               5                   10                  15

Ala Ile Ala Leu Pro Ala Tyr Gln Asp Tyr
            20                  25
```

(2) INFORMATION FOR SEQ ID NO: 10:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 10:

```
Ser Ser Gln Gln Ser Pro Ser Ala Gly Ser Glu Gln Gln Leu Asp Gln
1               5                   10                  15

Leu Leu Ala Met
            20
```